United States Patent
Carrow et al.

(10) Patent No.: US 10,266,623 B2
(45) Date of Patent: Apr. 23, 2019

(54) TRANSITION METAL CATALYSTS FOR OLEFIN POLYMERIZATION

(71) Applicant: THE TRUSTEES OF PRINCETON UNIVERSITY, Princeton, NJ (US)

(72) Inventors: Brad P. Carrow, Princeton, NJ (US); Wei Zhang, Exton, PA (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 15/322,347

(22) PCT Filed: Jun. 26, 2015

(86) PCT No.: PCT/US2015/038104
§ 371 (c)(1),
(2) Date: Dec. 27, 2016

(87) PCT Pub. No.: WO2015/200849
PCT Pub. Date: Dec. 30, 2015

(65) Prior Publication Data
US 2017/0137549 A1      May 18, 2017

Related U.S. Application Data

(60) Provisional application No. 62/018,263, filed on Jun. 27, 2014.

(51) Int. Cl.
*C08F 4/80* (2006.01)
*C08F 220/00* (2006.01)
*C08F 220/02* (2006.01)
*C08F 220/10* (2006.01)
*C08F 216/12* (2006.01)
*C08F 210/02* (2006.01)
*C08F 220/06* (2006.01)
*C08F 4/70* (2006.01)
*C08F 220/44* (2006.01)

(52) U.S. Cl.
CPC .......... *C08F 210/02* (2013.01); *C08F 4/7014* (2013.01); *C08F 4/80* (2013.01); *C08F 216/12* (2013.01); *C08F 220/00* (2013.01); *C08F 220/02* (2013.01); *C08F 220/06* (2013.01); *C08F 220/10* (2013.01); *C08F 220/44* (2013.01); *C08F 2410/01* (2013.01)

(58) Field of Classification Search
CPC ........ C08F 4/7014; C08F 4/80; C08F 218/10; C08F 220/00
See application file for complete search history.

(56) References Cited

U.S. PATENT DOCUMENTS 4,098,756 A      7/1978    Miller et al.

FOREIGN PATENT DOCUMENTS

WO      2013168626 A1    11/2013

OTHER PUBLICATIONS

International Search Report and Written Opinion of the International Application PCT/US2015/038104, dated Sep. 23, 2015, 8 pages.
Carrow, Brad P. et al., Transition-Metal-Catalyzed Functional Polyolefin Synthesis: Effecting Control through Chelating Ancillary Ligand Design and Mechanistic Insights; Macromolecules vol. 47, Mar. 19, 2014, pp. 2541-2555 [retrieved from internet, [retrieved on Dec. 23, 2013], http://pubs.acs.org/doi/abs/10.1021/ma500034g>.

*Primary Examiner* — Caixia Lu
(74) *Attorney, Agent, or Firm* — J. Clinton Wimbish; Nexsen Pruet, PLLC

(57) ABSTRACT

In one aspect, a chelating phosphine-phosphonic diamide (PPDA) ligand is described herein for constructing transition metal complexes operable for catalysis of olefin polymerization, including copolymerization of ethylene with polar monomer.

13 Claims, 7 Drawing Sheets

TRANSITION METAL CATALYSTS FOR OLEFIN POLYMERIZATION

RELATED APPLICATION DATA

This application is a U.S. National Phase of PCT/US2015/038104, filed Jun. 26, 2015, which claims priority under 35 U.S.C. § 119(e) to U.S. Provisional Patent Application Ser. No. 62/018,263 filed Jun. 27, 2014, each of which are incorporated herein by reference in their entireties.

STATEMENT OF GOVERNMENT RIGHTS

This invention was made with government support under Grant No. DMR-1420541 awarded by the National Science Foundation. The government has certain rights in the invention.

FIELD

The present invention relates to transition metal complexes and, in particular, to transition metal complexes operable for catalysis of olefin polymerization.

BACKGROUND

Free radical olefin polymerization is well-known and commercially important. However, copolymerizations of ethylene with polar industrial monomers, such as vinyl acetate and acrylic acid, are increasingly complex, requiring high temperature and exceedingly high pressures. Further, such processes intrinsically lack precise control over the resulting polymer architecture, polymer molecular weight and incorporation of polar monomer. In view of these deficiencies, coordination polymerization has been explored for potential controllable strategies for the synthesis of polyolefins having various functionalities derived from the incorporation of a polar monomer. Two dominant classes of transition metal catalysts have been developed to date for copolymerization of ethylene and industrial polar monomers. The first class encompasses group 10 complexes coordinated by an α-diimine ligand, commonly referred to Brookhart-type catalysts. The remaining class employs neutral palladium complexes coordinated by a phosphine sulfonate (Drent-type). These two classes have persistent limitations. For Brookhart catalysts, complex stability is limited for polymerizations conducted above room temperature. Even state-of-the-art Brookhart catalysts are persistent for only about 15 minutes at or above 90° C. While Drent catalysts generally exhibit greater thermal stability, they typically produce low-molecular weight copolymers of ethylene and polar industrial monomers and/or turnover with poor rates. Therefore, new transition metal catalysts are required for the production of polar functionalized polyolefins.

SUMMARY

In one aspect, a chelating phosphine-phosphonic diamide (PPDA) ligand is described herein for constructing transition metal complexes operable for catalysis of olefin polymerization, including copolymerization of ethylene with polar monomer. A PPDA ligand described herein is of Formula (I):

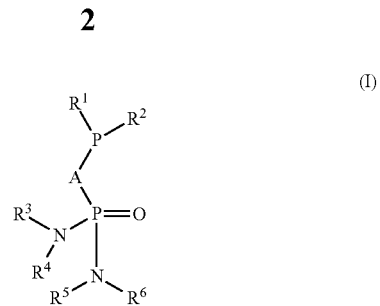

wherein A is selected from the group consisting of alkyl, alkenyl, aryl and heteroaryl and wherein $R^1$, $R^2$, $R^3$, $R^4$, $R^5$ and $R^6$ are independently selected from the group consisting of alkyl, heteroalkyl, cycloalkyl, heterocycloalkyl, aryl, heteroaryl, alkyl-aryl and alkyl-heteroaryl, wherein $R^1$ and $R^2$ may optionally form a ring structure and any combination of $R^3$, $R^4$, $R^5$ and/or $R^6$ may optionally form a ring structure.

In another aspect, transition metal complexes are described herein incorporating the PPDA ligand of Formula (I). Such transition metal complexes, in some embodiments, are suitable catalysts for copolymerization of ethylene with polar monomer. In some embodiments, a transition metal complex described herein is of Formula (II):

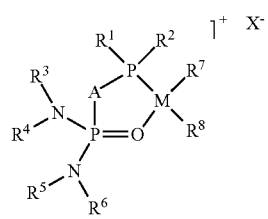

wherein M is a transition metal, A is selected from the group consisting of alkyl, alkenyl, aryl and heteroaryl and wherein $R^1$, $R^2$, $R^3$, $R^4$, $R^5$ and $R^6$ are independently selected from the group consisting of alkyl, heteroalkyl, cycloalkyl, heterocycloalkyl, aryl, heteroaryl, alkyl-aryl and alkyl-heteroaryl, wherein $R^1$ and $R^2$ may optionally form a ring structure and any combination of $R^3$, $R^4$, $R^5$ and/or $R^6$ may optionally form a ring structure and wherein $R^7$ is selected from the group consisting of alkyl and aryl and $R^8$ is selected from the group consisting of amine, heteroaryl, monophosphine, halo and sulfoxide and wherein $X^-$ is a non-coordinating counter anion.

Further, in some embodiments, a transition metal complex is of Formula (III):

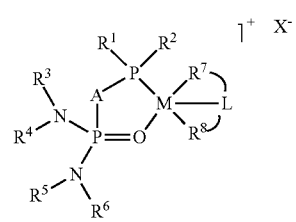

wherein M is a transition metal, A is selected from the group consisting of alkyl, alkenyl, aryl and heteroaryl, and wherein $R^1$, $R^2$, $R^3$, $R^4$, $R^5$ and $R^6$ are independently selected from the group consisting of alkyl, heteroalkyl, cycloalkyl, heterocycloalkyl, aryl, heteroaryl, alkyl-aryl and alkyl-heteroaryl, wherein $R^1$ and $R^2$ may optionally form a ring structure and any combination of $R^3$, $R^4$, $R^5$ and/or $R^6$ may optionally form a ring structure and $R^7$ and $R^8$ are moieties of a chelating alkyl or aryl ligand, L, and wherein $X^-$ is a non-coordinating counter anion. In some embodiments, for example, $R^7$ is an alkyl or aryl moiety and $R^8$ is a carbonyl or oxide moiety of ligand, L.

In a further aspect, methods of olefin polymerization are described herein. In some embodiments, a method of olefin polymerization comprises providing a reaction mixture of olefin monomer and transition metal complex of Formula (II) or Formula (III) and polymerizing the olefin monomer in the presence of the transition metal complex to provide polyolefin. Polymerization can proceed by coordination-insertion polymerization by which olefin monomer is added to the growing polymer chain through the transition metal complex of Formula (II) or Formula (III). In some embodiments, for example, suitable olefin monomer is ethylene or propylene.

In another aspect, methods of olefin copolymerization are described herein. A method of olefin copolymerization comprises providing a reaction mixture of olefin monomer, polar monomer and transition metal complex of Formula (II) or Formula (III) and copolymerizing the olefin monomer with the polar monomer in the presence of the transition metal complex. Copolymerization of the olefin and polar monomers can proceed by insertion or coordination polymerization through the transition metal complex. In some embodiments, suitable olefin monomer is ethylene or propylene and polar monomer is selected from acrylic acid, alkyl acrylic acids, alkyl acrylates, acetates, vinyl ethers, acrylamide, vinyl ethers and/or acrylonitrile. Moreover, as described further herein, polar monomer can be incorporated in-chain as opposed to incorporation at terminating end(s) of the copolymer.

Additionally, copolymer compositions are described herein. For example, a copolymer comprises olefin monomer and polar monomer, wherein greater than 50 percent of the polar monomer is positioned in-chain, and the copolymer has molecular weight ($M_w$) of at least 5,000 Da. In some embodiments, the copolymer has molecular weight of at least 10,000 Da or 20,000 Da. As described herein, suitable olefin monomer can be ethylene or propylene and polar monomer is selected from acrylic acid, alkyl acrylic acids, alkyl acrylates, acetates, vinyl ethers, acrylamide and/or acrylonitrile.

These and other embodiments are further described in the detailed description which follows.

DETAILED DESCRIPTION

Figure 1:
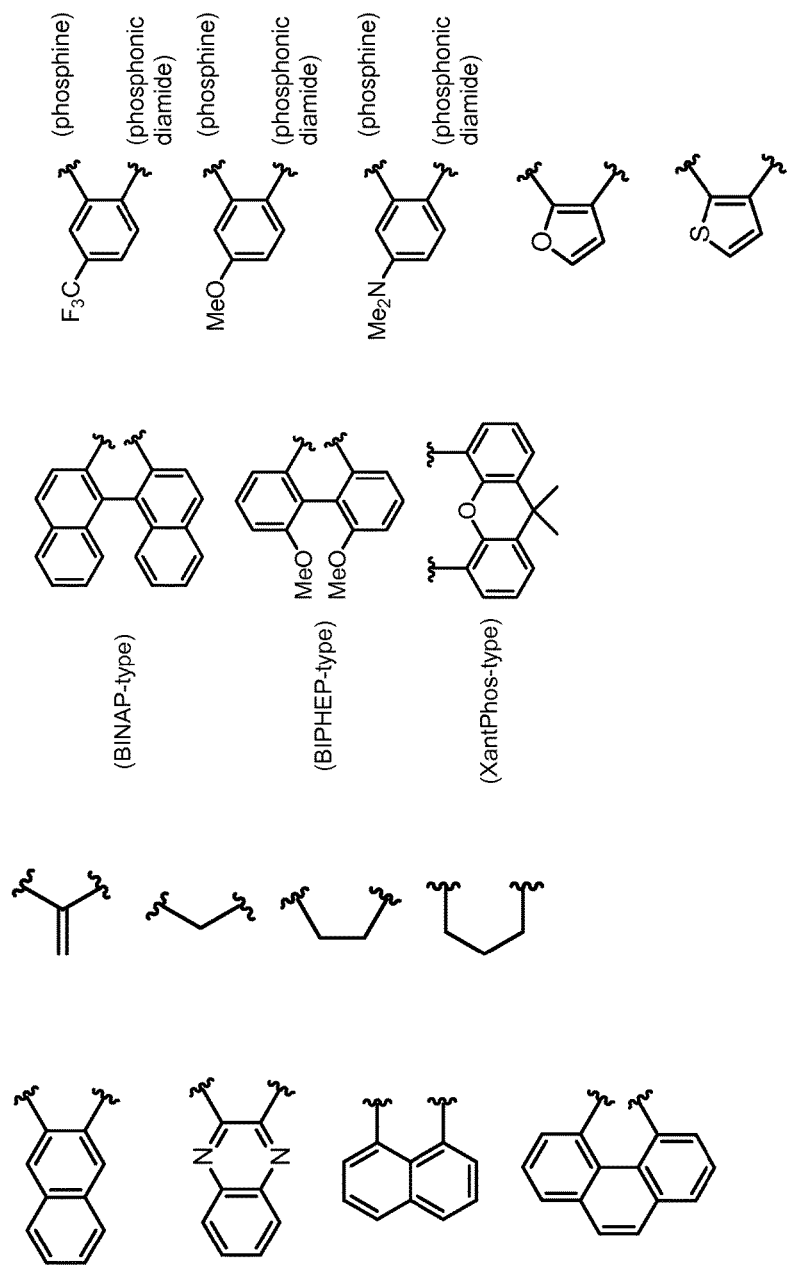
FIG. 1 illustrates chemical structures from which A of compounds described herein are selected according to some embodiments.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group optionally substituted with one or more substituents. For example, an alkyl can be $C_1$-$C_{30}$.

The term "alkenyl" as used herein, alone or in combination, refers to a straight or branched chain hydrocarbon group having at least one carbon-carbon double bond and optionally substituted with one or more substituents.

The term "aryl" as used herein, alone or in combination, refers to an aromatic monocyclic or multicyclic ring system optionally substituted with one or more ring substituents. For example, an aromatic monocyclic or multicyclic ring system may be substituted with one or more of alkyl, alkenyl, alkoxy, heteroalkyl and/or heteroalkenyl.

The term "heteroaryl" as used herein, alone or in combination, refers to an aromatic monocyclic or multicyclic ring system in which one or more of the ring atoms is an element other than carbon, such as nitrogen, oxygen and/or sulfur. The aromatic monocyclic or multicyclic ring system may further be substituted with one or more ring substituents, such as alkyl, alkenyl, alkoxy, heteroalkyl and/or heteroalkenyl.

The term "cycloalkyl" as used herein, alone or in combination, refers to a non-aromatic, saturated mono- or multicyclic ring system optionally substituted with one or more ring substituents.

The term "heterocycloalkyl" as used herein, alone or in combination, refers to a non-aromatic, saturated mono- or multicyclic ring system in which one or more of the atoms in the ring system is an element other than carbon, such as nitrogen, oxygen or sulfur, alone or in combination, and wherein the ring system is optionally substituted with one or more ring substituents.

The term "heteroalkyl" as used herein, alone or in combination, refers to an alkyl moiety as defined above, having one or more carbon atoms in the chain, for example one, two or three carbon atoms, replaced with one or more heteroatoms, which may be the same or different, where the point of attachment to the remainder of the molecule is through a carbon atom of the heteroalkyl radical.

The term "alkoxy" as used herein, alone or in combination, refers to the moiety RO—, where R is alkyl or alkenyl defined above.

I. PPDA Ligand

In one aspect, a chelating phosphine-phosphonic diamide (PPDA) ligand is described herein for constructing transition metal complexes operable for catalysis of olefin polymerization, including copolymerization of ethylene with polar monomer. A PPDA ligand described herein is of Formula (I):

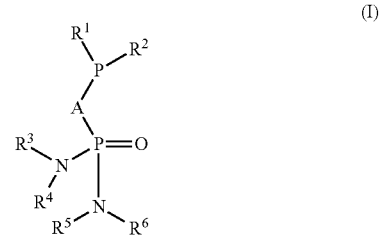

(I)

wherein A is selected from the group consisting of alkyl, alkenyl, aryl and heteroaryl and wherein $R^1$, $R^2$, $R^3$, $R^4$, $R^5$ and $R^6$ are independently selected from the group consisting of alkyl, heteroalkyl, cycloalkyl, heterocycloalkyl, aryl, heteroaryl, alkyl-aryl and alkyl-heteroaryl, wherein $R^1$ and $R^2$ may optionally form a ring structure and any combination of $R^3$, $R^4$, $R^5$ and/or $R^6$ may optionally form a ring structure.

Turning now to specific substituents of the PPDA ligand, A is selected from alkyl, alkenyl, aryl and heteroaryl. FIG. 1 illustrates various alkyl, alkenyl, aryl and heteroaryl structures from which A can be selected according to some embodiments described herein.

Figure 2:
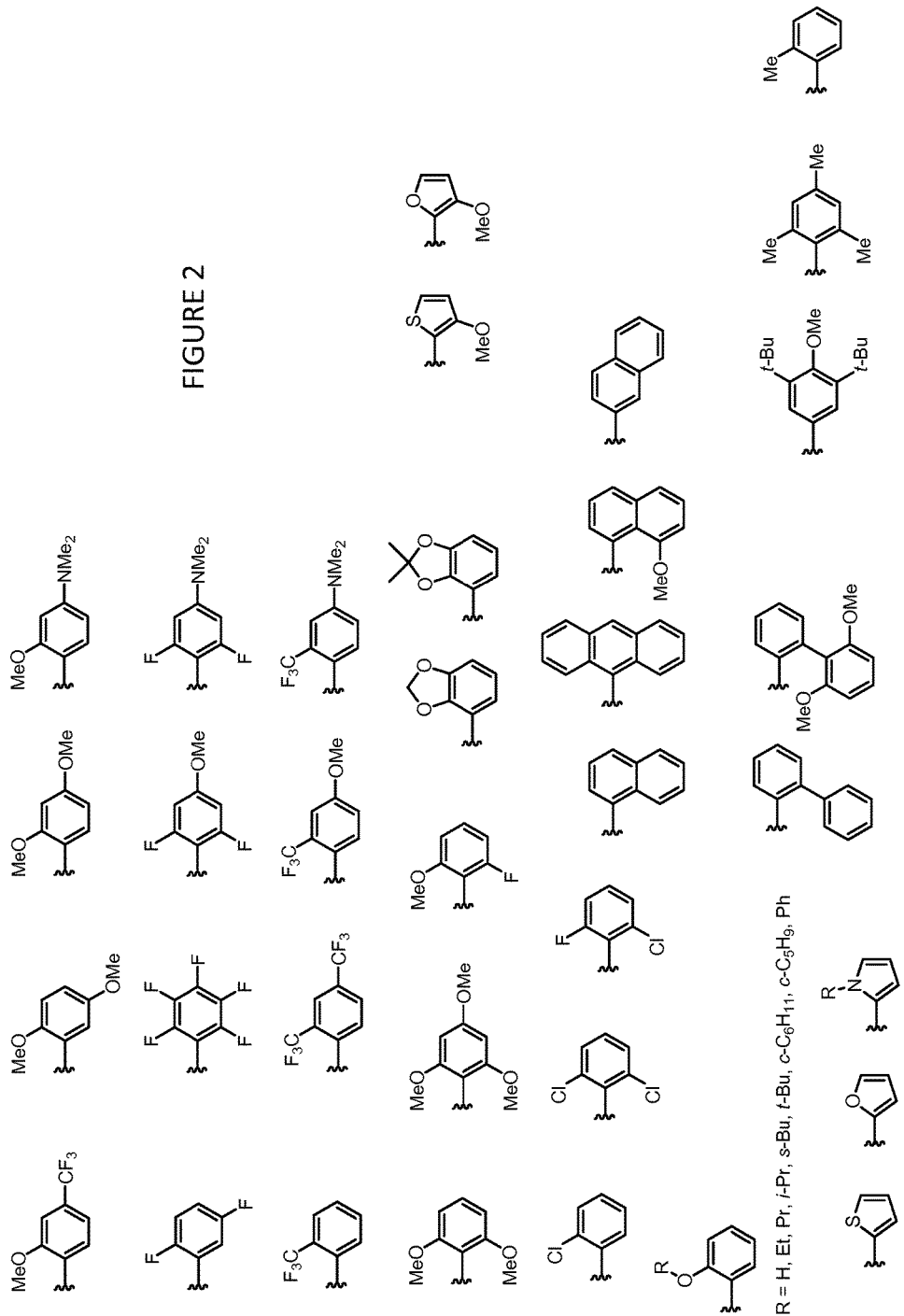
FIG. 2 illustrates aryl and heteroaryl chemical structures from which $R^1$ and/or $R^2$ of compounds described herein are independently selected according to some embodiments.
Figure 3:
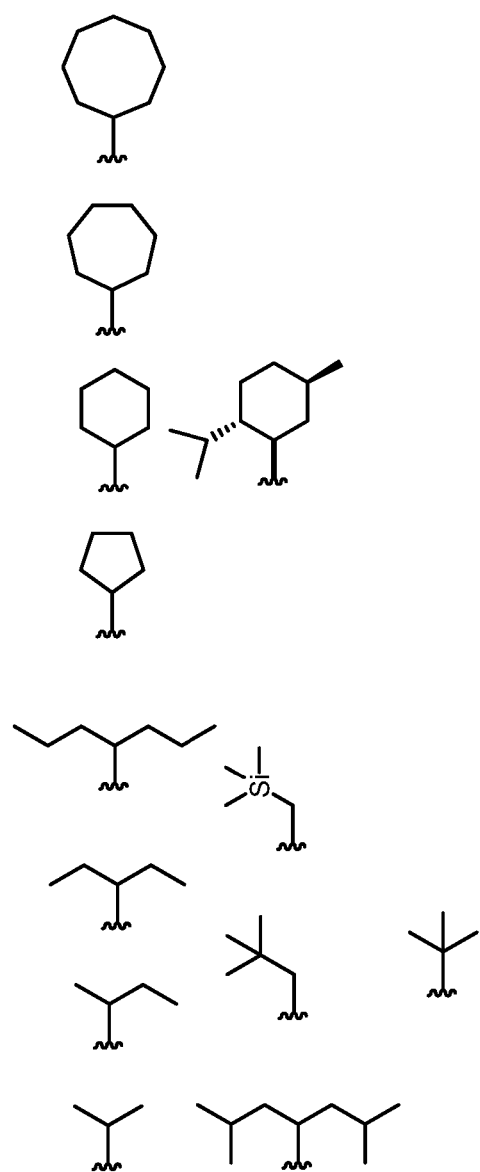
FIG. 3 illustrates alkyl, heteroalkyl and cycloalkyl chemical structures from which $R^1$ and/or $R^2$ of compounds described herein are independently selected according to some embodiments.
Figure 4:
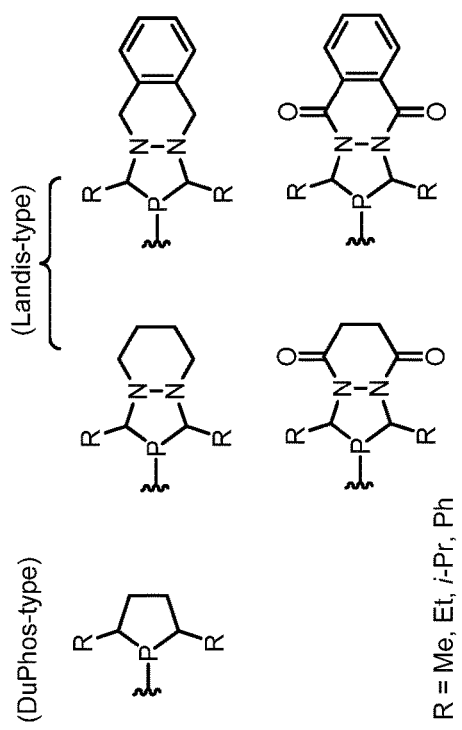
FIG. 4 illustrates ring or cyclized structures formed by the combination of $R^1$ and $R^2$ according to some embodiments described herein.

Moreover, $R^1$ and $R^2$ are independently selected from the group consisting of alkyl, heteroalkyl, cycloalkyl, heterocycloalkyl, aryl, heteroaryl, alkyl-aryl and alkyl-heteroaryl, wherein $R^1$ and $R^2$ may optionally form a ring structure. In some embodiments, aryl or heteroaryl of $R^1$ and/or $R^2$ are substituted with one or more ring substituents. Such substituents can include fluorinated alkyl, halide, alkoxy and heterocycloalkyl structures. In some embodiments, the substituents can be positioned ortho and/or para on the ring. FIG. 2 illustrates various substituted aryl and heteroaryl structures from which $R^1$ and/or $R^2$ can be independently selected according to some embodiments described herein. Additionally, $R^1$ and/or $R^2$ can be independently selected from alkyl, heteroalkyl and cycloalkyl. FIG. 3 illustrates alkyl, heteroalkyl and cycloalkyl structures from which $R^1$ and/or $R^2$ can be independently chosen according to some embodiments described herein. Further, $R^1$ and $R^2$ may form a ring structure. FIG. 4 illustrates ring structures formed by $R^1$ and $R^2$ according to some embodiments.

Figure 5:
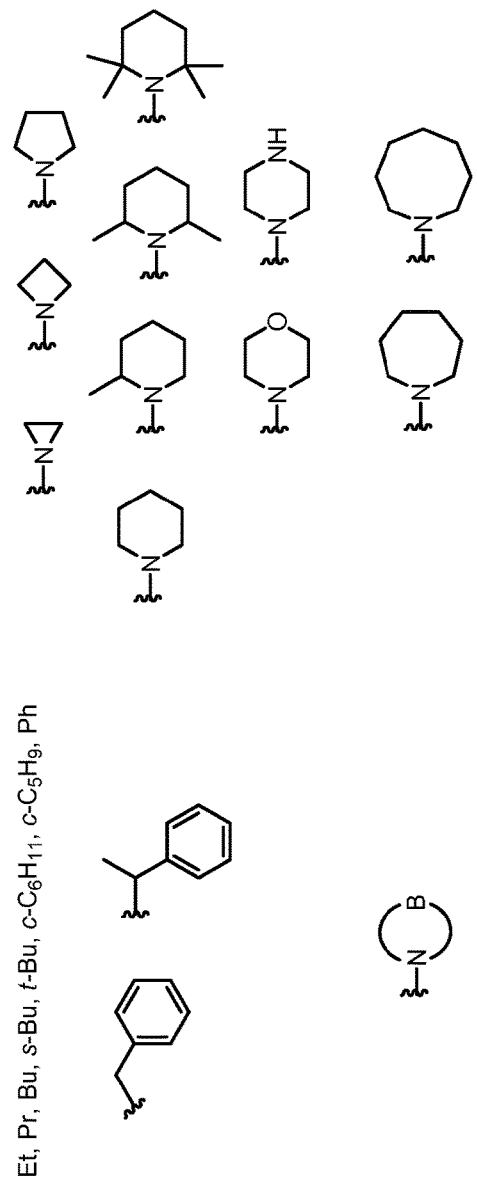
FIG. 5 illustrates alkyl, alkyl-aryl and heterocycloalkyl structures from which $R^3$, $R^4$, $R^5$ and/or $R^6$ are independently selected according to some embodiments.
Figure 6:
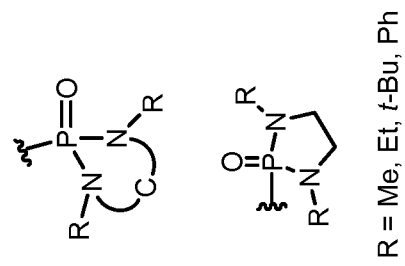
FIG. 6 illustrates ring or cyclized structures formed by various combinations of $R^3$, $R^4$, $R^5$ and/or $R^6$ according to some embodiments.

As described herein, $R^2$, $R^3$, $R^4$, $R^5$ and $R^6$ are independently selected from the group consisting of alkyl, heteroalkyl, cycloalkyl, heterocycloalkyl, aryl, heteroaryl, alkyl-aryl and alkyl-heteroaryl. FIG. 5 illustrates alkyl, heterocycloalkyl and alkyl-aryl structures from which $R^2$, $R^3$, $R^4$, $R^5$ and/or $R^6$ can be independently selected according to some embodiments described herein. Additionally, any combination of $R^3$, $R^4$, $R^5$ and/or $R^6$ may optionally form a ring structure. FIG. 6 illustrates ring structures formed by various combinations of $R^3$, $R^4$, $R^5$ and/or $R^6$ according to some embodiments.

II. Transition Metal Complexes

In another aspect, transition metal complexes are described herein incorporating the PPDA ligand of Formula (I). Such transition metal complexes, in some embodiments, are suitable catalysts for copolymerization of ethylene with polar monomer. In some embodiments, a transition metal complex described herein is of Formula (II):

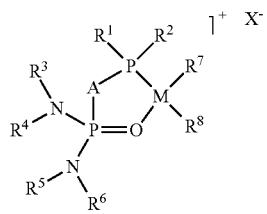

(II)

wherein M is a transition metal, A is selected from the group consisting of alkyl, alkenyl, aryl and heteroaryl and wherein $R^1$, $R^2$, $R^3$, $R^4$, $R^5$ and $R^6$ are independently selected from the group consisting of alkyl, heteroalkyl, cycloalkyl, heterocycloalkyl, aryl, heteroaryl, alkyl-aryl and alkyl-heteroaryl, wherein $R^1$ and $R^2$ may optionally form a ring structure and any combination of $R^3$, $R^4$, $R^5$ and/or $R^6$ may optionally form a ring structure and wherein $R^7$ is selected from the group consisting of alkyl and aryl and $R^8$ is selected from the group consisting of amine, heteroaryl, monophosphine, halo and sulfoxide and wherein $X^-$ is a non-coordinating counter anion.

Further, in some embodiments, a transition metal complex is of Formula (III):

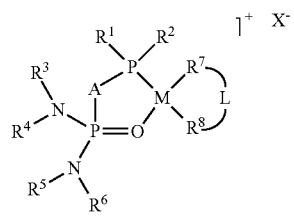

(III)

wherein M is a transition metal, A is selected from the group consisting of alkyl, alkenyl, aryl and heteroaryl, and wherein $R^1$, $R^2$, $R^3$, $R^4$, $R^5$ and $R^6$ are independently selected from the group consisting of alkyl, heteroalkyl, cycloalkyl, heterocycloalkyl, aryl, heteroaryl, alkyl-aryl and alkyl-heteroaryl, wherein $R^1$ and $R^2$ may optionally form a ring structure and any combination of $R^3$, $R^4$, $R^5$ and/or $R^6$ may optionally form a ring structure and $R^7$ and $R^8$ are moieties of a chelating alkyl or aryl ligand, L, and wherein $X^-$ is a non-coordinating counter anion. In some embodiments, for example, $R^7$ is an alkyl or aryl moiety and $R^8$ is a carbonyl or oxide moiety of ligand, L.

In some embodiments, A and $R^1$, $R^2$, $R^3$, $R^4$, $R^5$ and $R^6$ can be selected from any of the structures illustrated in FIGS. 1-6 as described in Section I above. Further, $X^-$ is a non-coordinating counter anion, which preferably exhibits suitable organic solvent solubility. Suitable non-coordinating counter anions can include borates and aluminates. In some embodiments, for example, $X^-$ is selected from the group consisting of $[B[3,5-(CF_3)_2C_6H_3]_4]^-$ also designated as $[BAr^F_4]^-$, $[B(C_6F_5)_4]^-$, $Al[OC(CF_3)_3]_4^-$, $SbF_6$ and $PF_6$.

M can be any transition metal not inconsistent with the objectives of the present invention. For example, in some embodiments, M is selected from Group 10 of the Periodic Table consisting of nickel, palladium and platinum. However, M can also be selected from earlier group(s) of transition metal elements. Examples 2 and 3 hereinbelow provide several transition metal complexes of Formulas (II) and (III) respectively wherein palladium is the transition metal.

III. Methods of Polymerization

In a further aspect, methods of olefin polymerization are described herein. In some embodiments, a method of olefin polymerization comprises providing a reaction mixture of olefin monomer and transition metal complex of Formula (II) or Formula (III) and polymerizing the olefin monomer in the presence of the transition metal complex to provide polyolefin. Polymerization can proceed by coordination-insertion polymerization by which olefin monomer is added to the growing polymer chain through the transition metal complex of Formula (II) or Formula (III). In some embodiments, for example, suitable olefin monomer is ethylene or propylene. Moreover, in some embodiments, polymerization of olefin monomer can proceed in the presence of various contaminants that prior transition metal catalyst cannot tolerate. In some embodiments, polymerization of olefin monomer by transition metal complexes of Formulas (II) and/or (III) can proceed in the presence of diethyl ether, ethylacetate and/or other similar species found in dirty ethylene streams.

In another aspect, methods of olefin copolymerization are described herein. A method of olefin copolymerization comprises providing a reaction mixture of olefin monomer, polar monomer and transition metal complex of Formula (II) or Formula (III) and copolymerizing the olefin monomer with the polar monomer in the presence of the transition metal complex. Copolymerization of the olefin and polar monomers can proceed by insertion or coordination polymerization through the transition metal complex. In some embodiments, suitable olefin monomer is ethylene or propylene and polar monomer is selected from acrylic acid, alkyl acrylic acids, alkyl acrylates, alkenyl acetates, acrylamide, vinyl ethers and/or acrylonitrile. Moreover, as described further below with reference to Table II, polar monomer can be incorporated in-chain as opposed to incorporation at terminating end(s) of the copolymer.

Figure 7:
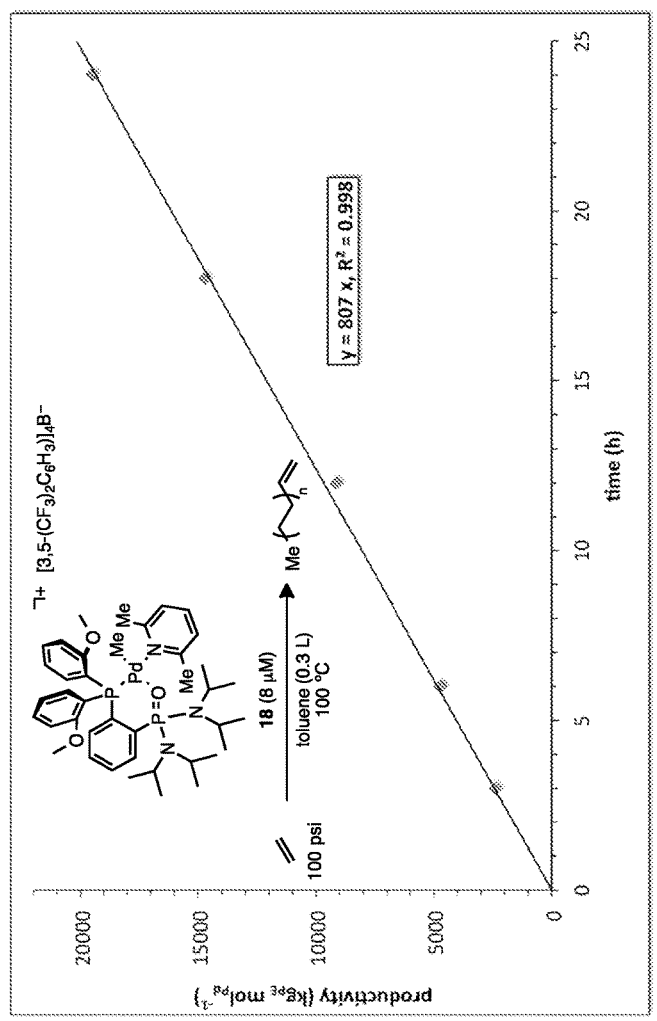
FIG. 7 is a plot of productivity versus time for homopolymerization of ethylene by a transition metal complex of Formula (II) according to one embodiment described herein.

Importantly, transition metal complexes of Formula (II) and/or Formula (III) can exhibit marked thermal stability often persisting for at least 24 hours at 100° C. during polymerization of ethylene. Such thermal stability allows transition metal complexes described herein to provide homopolymers and copolymers of molecular weight in excess of 10,000 Da, a threshold generally allowing for desirable physical properties. In some embodiments, homopolymers and copolymers produced according to methods described herein have molecular weight of 10,000-250,000. FIG. 7, for example, is a plot of productivity versus time for homopolymerization of ethylene by a transition metal complex of Formula (II) according to one embodiment described herein. The transition metal complex is 18 described in the following Examples.

Additionally, copolymer compositions are described herein. For example, a copolymer comprises olefin monomer and polar monomer, wherein greater than 50 percent of the polar monomer is positioned in-chain, and the copolymer has molecular weight ($M_w$) of at least 5,000 Da or at least 10,000 Da. As used herein, "in-chain" refers to distribution of the polar monomer along interior regions or positions of the polymeric chain, as opposed to incorporation of polar monomer at the ends of the polymeric chain. The ability to distribute polar monomer in-chain provides unique properties to the resultant copolymer. For example, in-chain distribution of polar monomer can provide the copolymer enhanced gas barrier properties. In some embodiments, such copolymer can exhibit enhanced barrier properties to oxygen and/or other degradative gases, thereby enabling use of the copolymer in various gas barrier applications such as food packaging, barrier films for electronics and substrates for dye-sensitized photovoltaics and/or thin film transistors.

Moreover, in-chain distribution of polar monomer can enhance adhesion characteristics of the copolymer relative to polyolefins, such as LDPE and HDPE Enhanced adhesion characteristics expand compatibility of the copolymer with a variety of materials including dyes and/or other polar polymeric species and coatings. Therefore, copolymer described herein can serve as a bulk structural material for various laminate and/or surface coated architectures without the requirement of special surface pretreatments, such as exposure to peroxide or plasma, to render the surface hydrophilic. In-chain polar monomer can also serve as locations for anchoring various species to the copolymer. For example, various biological molecules including amino acids and peptides may be attached via exposed functional groups of the copolymer leading to biological molecule immobilization. In additional aspect, in-chain polar monomer can permit copolymer described herein to serve as a compatibilizing agent for polymer blends. In some embodiments, the copolymer can inhibit phase separation in a mixture of two or more immiscible polymeric species.

In some embodiments, copolymer having in-chain polar monomer has molecular weight selected from Table I:

TABLE I

| Copolymer Molecular Weight ($M_w$) Da |
|---|
| ≥20,000 |
| ≥30,000 |
| ≥40,000 |
| ≥50,000 |
| ≥100,000 |
| 10,000-200,000 |

Additionally, percentage of polar monomer of the copolymer incorporated in-chain can be selected from Table II. As provided in Table II, polar monomer, in some embodiments, is exclusively incorporated in-chain.

TABLE II

| Polar Monomer In-chain (%) |
|---|
| ≥60 |
| ≥70 |
| ≥80 |
| ≥90 |
| ≥95 |
| ≥99 |
| 100 |
| 50-100 |

Further, mol. % of polar monomer incorporated into the copolymer can be selected from Table III.

TABLE III

| mol. % Polar Monomer Incorporated into Copolymer |
|---|
| 0.5-15 |
| 3-15 |
| 3-10 |
| 3-8 |
| 5-15 |
| 5-10 |
| 10-15 |

As described herein, suitable olefin monomer can be ethylene and/or propylene and polar monomer is selected from acrylic acid, alkyl acrylic acids, alkyl acrylates, acetates, acrylamide, vinyl ethers and/or acrylonitrile.

These and other embodiments are further illustrated by the following non-limiting examples.

Example 1—Synthesis of PPDA Ligands

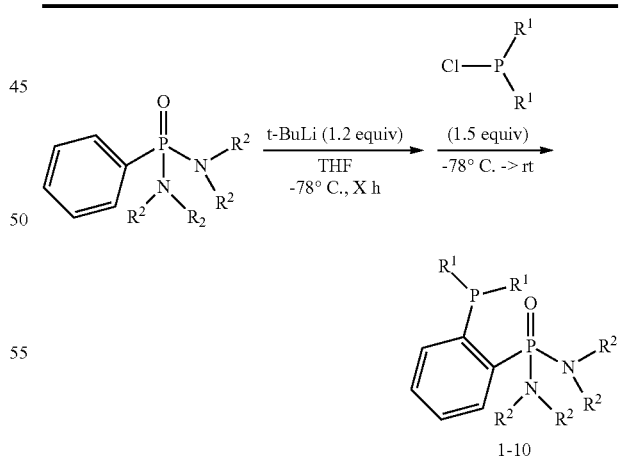

| entry | compound | $R^1$ | $R^2$ | yield (%) |
|---|---|---|---|---|
| 1 | 1 | i-$C_3H_7$ | $CH_3$ | —[a] |
| 2 | 2 | 2-($CH_3O$)$C_6H_4$ | $CH_3$ | 52 |
| 3 | 3 | i-$C_3H_7$ | i-$C_3H_7$ | 69 |
| 4 | 4 | i-$C_6H_{11}$ | i-$C_3H_7$ | 74 |
| 5 | 5 | $C_6H_5$ | i-$C_3H_7$ | 92 |

| 6  | 6  | 2-FC$_6$H$_4$                   | i-C$_3$H$_7$ | 15 |
| 7  | 7  | 2,6-F$_2$C$_6$H$_3$             | i-C$_3$H$_7$ | 35 |
| 8  | 8  | 2(CH$_3$O)C$_6$H$_4$            | i-C$_3$H$_7$ | 75 |
| 9  | 9  | 2-furyl                         | i-C$_3$H$_7$ | 43 |
| 10 | 10 | 2-(CF$_3$O)C$_6$H$_4$           | i-C$_3$H$_7$ | 24 |

[a]Used directly without isolation.

Representative synthesis of a PPDA ligand: N,N,N',N'-tetraisopropyl 2-[bis(2-methoxyphenyl)phosphino]phenylphosphonic diamide (8). To a solution of N,N,N',N'-tetraisopropyl phenylphosphonic diamide (0.65 g, 2.0 mmol) in THF (30 mL) was added tert-butyllithium (1.4 mL, 2.4 mmol, 1.7 M in pentane) at −78° C. The mixture was then warmed to −30° C. and stirred for 3 h. A THF solution of bis(2-methoxyphenyl)chlorophosphine (0.84 g, 3.0 mmol) was added to the reaction mixture and then stirred for 30 min after slowly warming to room temperature. Evaporation of solvent and purification of the residue by column chromatography (ethyl acetate/hexane) gave 0.85 g (75%) of 8 as a white solid. $^1$H NMR (500 MHz, CDCl$_3$) δ 7.85 (ddd, J=11, 7, 4 Hz, 1H), 7.32 (td, J=7, 3 Hz, 1H), 7.26 (t, J=11 Hz, 3H), 7.07 (dt, J=7, 3 Hz, 1H), 6.85 (dd, J=8, 4 Hz, 2H), 6.78 (t, J=7 Hz, 2H), 6.60 (s, 2H), 3.78-3.65 (m, 10H), 1.32 (d, J=7 Hz, 12H), 1.23 (d, J=7 Hz, 12H). $^{31}$P NMR (121 MHz, CDCl$_3$) δ 29.5, −25.8. $^{13}$C NMR (125 MHz, CDCl$_3$) δ 160.9, 143.7, 140.2, 135.5, 134.2, 133.2, 130.1, 129.0, 128.1, 126.5, 120.5, 110.0, 55.2, 46.6, 24.2. HRMS (ESI) m/z Calc'd for C$_{32}$H$_{46}$N$_2$O$_3$P$_2$+H (M+H) 569.3062, Found 569.3094.

Compound 2 was prepared in an analogous way as for 8; 0.65 g (52%) of 2 was obtained as a white solid. $^1$H NMR (500 MHz, CDCl$_3$) δ 8.24 (ddd, J=11, 8, 3 Hz, 1H), 7.44 (td, J=7, 3 Hz, 1H), 7.37-7.27 (m, 3H), 7.06 (d, J=7 Hz, 1H), 6.88 (d, J=8 Hz, 2H), 6.83 (td, J=7, 3 Hz, 2H), 6.56 (s, 2H), 3.68 (s, 6H), 2.70-2.34 (m, 12H). $^{31}$P NMR (203 MHz, CDCl$_3$) δ 30.9, −27.7. $^{13}$C NMR (126 MHz, CDCl$_3$) δ 160.9, 141.3, 137.4, 136.0, 135.1, 134.1, 131.2, 129.9, 128.4, 125.6, 121.0, 109.9, 55.4, 36.8. HRMS (ESI) m/z Calc'd for C$_{24}$H$_{30}$N$_2$O$_3$P$_2$+H (M+H) 457.1810, Found 457.1802.

Example 2—Synthesis of Cationic (PPDA)(Methyl)(Lutidine)Palladium Complexes

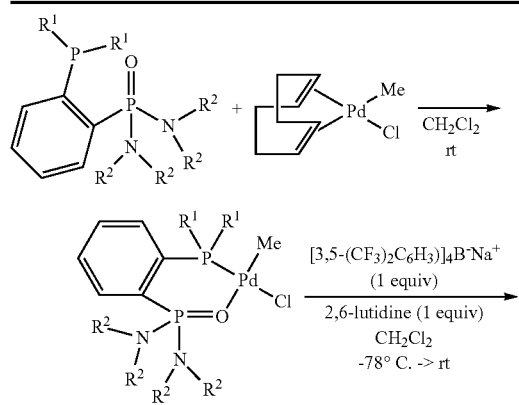

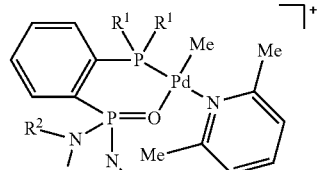

[3,5-(CF$_3$)$_2$C$_6$H$_3$)]$_4$B$^-$ 11-20

| entry | compound | R$^1$ | R$^2$ | yield (%) |
|---|---|---|---|---|
| 1  | 11 | i-C$_3$H$_7$              | CH$_3$        | 89 |
| 2  | 12 | 2-(CH$_3$O)C$_6$H$_4$     | CH$_3$        | 84 |
| 3  | 13 | i-C$_3$H$_7$              | i-C$_3$H$_7$  | 86 |
| 4  | 14 | i-C$_5$H$_{11}$           | i-C$_3$H$_7$  | 90 |
| 5  | 15 | C$_6$H$_5$                | i-C$_3$H$_7$  | 85 |
| 6  | 16 | 2-FC$_6$H$_4$             | i-C$_3$H$_7$  | 81 |
| 7  | 17 | 2,6-F$_2$C$_6$H$_3$       | i-C$_3$H$_7$  | 92 |
| 8  | 18 | 2-(CH$_3$O)C$_6$H$_4$     | i-C$_3$H$_7$  | 65 |
| 9  | 19 | 2-furyl                   | i-C$_3$H$_7$  | 92 |
| 10 | 20 | 2-(CF$_3$O)C$_6$H$_4$     | i-C$_3$H$_7$  | 88 |

Representative synthesis of a (PPDA)palladium catalyst: [(8-κ-P,κ-O)(methyl)(2,6-lutidine)palladium]{tetrakis[3,5-bis(trifluoromethyl)phenyl]borate} (18). (1,5-cyclooctadiene)(chloro)(methyl)palladium (178 mg, 0.67 mmol) and 8 (381 mg, 0.67 mol) were weighed into a small vial. The mixture was dissolved in dichloromethane (5 mL) at room temperature, and the solution was stirred for 10 min. The total volume was reduced to ca. 2 mL under reduced pressure and then diluted with toluene (10 mL). After standing overnight, the mother liquor was decanted, the solids were washed with toluene and pentane then dried under vacuum to afford 409 mg of (8-κ-P,κ-O)(chloro)(methyl)palladium.

(8-κ-P,κ-O)(chloro)(methyl)palladium (80 mg, 0.11 mmol) and 2,6-lutidine (13 mg, 0.12 mmol) were weighed into a small vial and dissolved in dichloromethane (5 mL). The solution was then added to a flask containing sodium tetrakis[3,5-bis(trifluoromethyl)phenyl]borate (98 mg, 0.11 mmol) cooled to −78° C. The mixture was slowly warmed to rt with vigorous stirring. Stirring was continued for an additional 30 min at rt. The solids were removed by filtration through Celite, the filtrate wag concentrated to ca. 2 mL, and then diluted with toluene (10 mL). After standing overnight, the precipitate was filtered and washed with pentane then dried under vacuum to afford 119 mg (65%) of 18 as a pale yellow solid. $^1$H NMR (500 MHz, CD$_2$Cl$_2$) δ 8.68 (dd, J=16, 8 Hz, 1H), 7.90 (ddd, J=15, 8, 5 Hz, 1H), 7.82 (s, 8H), 7.71 (dd, J=15, 10 Hz, 2H), 7.67-7.60 (m, 6H), 7.52 (t, J=8 Hz, 1H), 7.35-7.22 (m, 4H), 7.12 (dd, J=8, 6 Hz, 1H), 7.06-6.97 (m, 2H), 6.77 (dd, J=12, 8 Hz, 1H), 3.78 (s, 3H), 3.70-3.61 (m, 2H), 3.53 (s, 3H), 3.49-3.41 (m, 2H), 3.31 (s, 3H), 3.18 (s, 3H), 1.16 (d, J=7 Hz, 6H), 1.05 (d, J=7 Hz, 6H), 1.02 (d, J=7 Hz, 6H), 0.93 (d, J=7 Hz, 6H), 0.00 (d, J=3 Hz, 3H). $^{31}$P NMR (121 MHz, CD$_2$Cl$_2$) δ 30.2, 24.9. $^{19}$F NMR (300 MHz, CD$_2$Cl$_2$) δ −62.9. $^{13}$C NMR (125 MHz, CD$_2$Cl$_2$) δ 161.7, 159.2, 158.6, 140.6, 138.5, 137.8, 136.8, 136.6, 135.0, 134.8, 134.0, 133.6, 133.0, 129.9, 129.3, 129.2, 128.9, 128.8, 125.2, 124.6, 122.7, 121.3, 120.6, 117.4, 116.0, 115.3, 111.7, 111.1, 54.9, 47.5, 47.3, 26.4, 24.2, 23.6, 22.7, 22.1, −2.8.

Example 3—Synthesis of Cationic (PPDA)[2-Ac-etanilido-κ-C,κ-O]Palladium Complexes

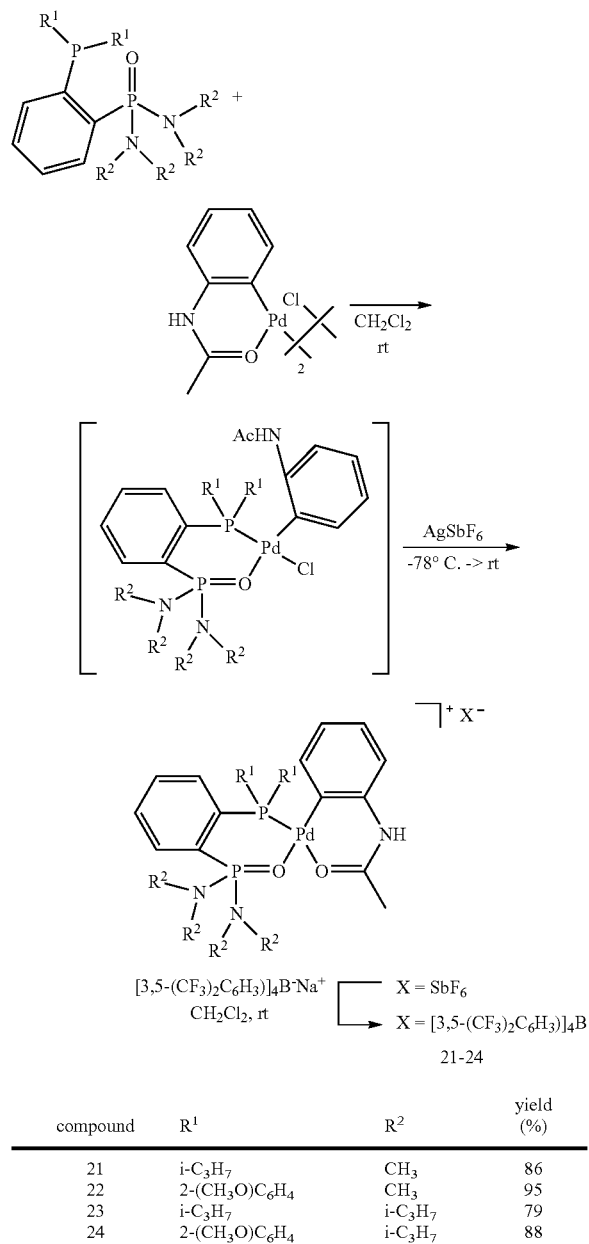

| compound | R$^1$ | R$^2$ | yield (%) |
|---|---|---|---|
| 21 | i-C$_3$H$_7$ | CH$_3$ | 86 |
| 22 | 2-(CH$_3$O)C$_6$H$_4$ | CH$_3$ | 95 |
| 23 | i-C$_3$H$_7$ | i-C$_3$H$_7$ | 79 |
| 24 | 2-(CH$_3$O)C$_6$H$_4$ | i-C$_3$H$_7$ | 88 |

Representative Synthesis of a (PPDA)Palladium Catalyst: {(8-κ-P,κ-O){2-[(acetyl-κ-O)amino]phenyl-κC} palladium} {tetrakis[3,5-bis(trifluoromethyl)phenyl]borate}(24)

Bis[μ-(chloro)]bis[2-[(acetyl-κ-O)amino]phenyl-κ-C]dipalladium (111 mg, 0.40 mmol) and 8 (228 mg, 0.40 mmol) were weighed into a vial and CH$_2$Cl$_2$ (5 mL) was then added. The suspension was stirred at room temperature for 3 h. The solution was filtered through Celite, the filtrate was concentrated to ca. 2 mL, and the solution was diluted with toluene (10 mL). After standing overnight, the precipitate was filtered, washed with pentane, and then dried under vacuum to afford 241 mg of (8-κ-P,κ-O)[2-(N-acetylamino) phenyl](chloro)palladium as a yellow solid.

(8-κ-P,κ-O)[2-(N-acetylamino)phenyl](chloro)palladium (137 mg, 0.16 mmol) was dissolved in CH$_2$Cl$_2$ (5 mL) and the solution was added to a flask containing AgSbF$_6$ (56 mg, 0.16 mmol) cooled to −78° C. The mixture was slowly warmed to room temperature over 30 min. The solids were removed by filtration through Celite, the filtrate was concentrated to ca. 2 mL, and the solution was diluted with toluene (10 mL). After standing overnight, the precipitate was filtered, washed with pentane, and dried under vacuum to afford 135 mg of {(8-κ-P,κ-O)[2-[(acetyl-κ-O) amino]phenyl-κ-C]palladium} {SbF$_6$} as a yellow solid.

{(8-κ-P,κ-O)[2-[(acetyl-κ-O)amino]phenyl-κ-C]palladium} {SbF$_6$} (74 mg, 0.069 mmol) and sodium tetrakis[3,5-bis(trifluoromethyl)phenyl]borate (62 mg, 0.069 mmol) were weighed into a vial. CH$_2$Cl$_2$ (5 mL) was then added, and the mixture was stirred for 15 min. The solids were removed by filtration through Celite, the filtrate was concentrated to ca. 2 mL, and then diluted with pentane (10 mL). After standing overnight, the precipitate was filtered, washed with pentane, and dried under vacuum to afford 102 mg (88%) of 24 as a yellow solid. $^1$H NMR (500 MHz, CD$_2$Cl$_2$) δ 8.77 (s, 1H), 7.86 (s, 1H), 7.71-7.62 (m, 1H), 7.58 (s, 8H), 7.48 (t, J=8 Hz, 1H), 7.42 (s, 4H), 7.40-7.30 (m, 2H), 7.29-7.17 (m, 2H), 7.12-7.05 (m, 1H), 6.82-6.72 (m, 2H), 6.67 (d, J=8 Hz, 1H), 6.55 (t, J=8 Hz, 1H), 6.48-6.40 (m, 1H), 6.38 (dd, J=8, 2 Hz, 1H), 6.26 (t, J=8 Hz, 1H), 5.99 (t, J=8 Hz, 1H), 3.64-3.49 (m, 2H), 3.47-3.21 (m, 5H), 3.17 (s, 3H), 2.21 (s, 3H), 1.25 (d, J=7 Hz, 6H), 1.01 (d, J=7 Hz, 6H), 0.98 (d, J=7 Hz, 6H), 0.73 (d, J=7 Hz, 6H). $^{31}$P NMR (203 MHz, CD$_2$Cl$_2$) δ 30.9, 28.3. $^{13}$C NMR (125 MHz, CD$_2$Cl$_2$) δ 169.4, 161.8, 141.1, 140.0, 137.2, 136.7, 136.6, 136.0, 159.6, 134.7, 133.8, 133.5, 133.1, 132.6, 132.2, 130.5, 130.4, 129.7, 129.6, 128.8, 127.5, 124.63, 124.58, 123.8, 121.8, 120.7, 117.5, 115.0, 112.1, 111.4, 54.8, 47.8, 47.5, 23.7, 22.5, 22.1, 22.0.

Example 4—Polymerization of Ethylene by a (PPDA)Pd Complex

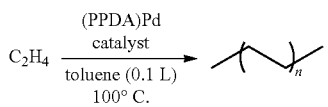

$$C_2H_4 \xrightarrow[\text{toluene (0.1 L)}]{\text{(PPDA)Pd catalyst}} \text{polymer}$$
100° C.

| Entry | catalyst (μM) | C$_2$H$_4$ (bar) | time (min) | yield (g) | activity [kg (mol Pd)$^{-1}$ h$^{-1}$] | M$_w$$^a$ (Da) | Đ (M$_w$/M$_n$)$^a$ | Me br$^b$ |
|---|---|---|---|---|---|---|---|---|
| 1 | 11 (25) | 30 | 60 | 7.14 | 2,900 | 5,200 | 1.8 | 0.5 |
| 2$^c$ | 12 (50) | 30 | 30 | 1.53 | 4,600 | 37,000 | 5.1 | 21 |
| 3 | 12 (12.5) | 30 | 15 | 0.95 | 3,100 | 160,000 | 2.0 | n.d.$^d$ |
| 4 | 12 (25) | 30 | 15 | 3.60 | 5,800 | 120,000 | 1.6 | 1.4 |

-continued

| | | | | | | | | |
|---|---|---|---|---|---|---|---|---|
| 5 | 12 (25) | 15 | 30 | 3.56 | 2,800 | 130,000 | 1.6 | 2.9 |
| 6 | 12 (25) | 7 | 30 | 2.48 | 2,000 | 100,000 | 1.5 | 2.7 |
| 7 | 12 (25) | 3.5 | 30 | 1.19 | 950 | 21,000 | 2.5 | 7.0 |
| 8 | 13 (25) | 30 | 15 | 1.08 | 1,700 | 39,000 | 1.6 | 2.5 |
| 9 | 14 (25) | 23 | 30 | 2.60 | 1,000 | 81,000 | 1.4 | 16 |
| 10 | 15 (25) | 30 | 30 | trace | — | — | — | — |
| 11 | 16 (25) | 30 | 60 | 4.80 | 1,900 | 88,000 | 1.5 | n.d.[d] |
| 12 | 17 (25) | 30 | 15 | 6.30 | 10,000 | 80,000 | 1.8 | 3.0 |
| 13[c] | 18 (50) | 30 | 30 | 1.74 | 5,700 | 26,000 | 5.7 | n.d.[d] |
| 14 | 18 (25) | 30 | 15 | 1.35 | 2,200 | 240,000 | 1.4 | 13 |
| 15 | 18 (25) | 3.5 | 120 | 1.35 | 270 | 16,000 | 1.6 | 21 |
| 16 | 19 (25) | 30 | 60 | 1.45 | 580 | 1,400 | 1.7 | n.d.[d] |
| 17 | 20 (25) | 30 | 30 | trace | — | — | — | — |
| 18 | 24 (25) | 30 | 30 | 0.19 | 160 | 160,000 | 1.3 | n.d.[d] |
| 19 | 30 (12.5) | 30 | 15 | 0.52 | 1,700 | 140,000 | 1.3 | 4 |
| 20 | 31 (12.5) | 30 | 15 | 2.12 | 6,800 | 120,000 | 1.4 | 7 |

[a]Absolute molecular weight and polydispersity determined by GPC analysis with triple detection.
[b]Methyl branches per 1000 carbons as determined by $^1$H or quantitative $^{13}$C NMR spectroscopy.
[c]Reaction conducted in a 7-well autoclave; 10 mL total volume.
[d]Not determined.

Example 5—Copolymerization of Ethylene and Polar Monomer Catalyzed by a (PPDA)Pd Complex

| Entry | catalyst (mM) | R (M) | time (h) | yield (g) | activity [kg (mol Pd)$^{-1}$ h$^{-1}$] | $M_w$[a] (Da) | Đ ($M_w/M_n$) | Me br[b] | χ[c] (%) |
|---|---|---|---|---|---|---|---|---|---|
| 1 | 12 (0.67) | CO$_2$H (1.5) | 15 | 0.66 | 4.4 | 31,000 | 2.9 | 1.2 | 2.7 |
| 2[d] | 12 (0.67) | CO$_2$Me (2.2) | 12 | 0.27 | 2.2 | 21,000 | 1.4 | 7.4 | 2.0 |
| 3 | 12 (0.67) | CO$_2$Me (2.2) | 15 | 1.48 | 9.9 | 74,000 | 1.6 | 2.1 | 0.7 |
| 4 | 17 (0.67) | CO$_2$Me (2.2) | 9 | 0.83 | 9.2 | 9,100 | 3.5 | n.d.[e] | n.d.[e] |
| 5 | 18 (0.67) | CO$_2$Me (2.2) | 13 | 0.32 | 2.4 | 29,000 | 1.4 | 4.8 | 1.3 |
| 6 | 23 (0.69) | CH$_2$OAc (1.6) | 15 | 0.97 | 6.2 | 23,000 | 2.1 | 2.5 | 1.0 |
| 7 | 12 (0.67) | CH$_2$OAc (1.6) | 12 | 0.79 | 6.6 | 4,900 | 4.5 | n.d.[e] | 1.2 |
| 8 | 17 (0.67) | CO$_2$Me (2.2) | 9 | 0.83 | 9.2 | 9,000 | 3.5 | 4.7 | 1.8 |
| 9[f] | 30 (0.70) | CO$_2$Me (2.2) | 12 | 1.03 | 8.3 | 19,000 | 1.5 | n.d.[e] | 3.7 |
| 10[f] | 31 (0.86) | CO$_2$Me (2.2) | 12 | 4.11 | 26 | 34,000 | 1.8 | n.d.[e] | 8.6 |

[a]Absolute molecular weight and polydispersity determined by GPC analysis with triple detection.
[b]Methyl branches per 1000 carbons as determined by $^1$H NMR spectroscopy.
[c]Mole fraction of polar monomer incorporated into the product as determined by $^1$H NMR spectroscopy.
[d]95° C.
[e]Not determined.
[f]100° C.

Representative procedure for polymerizations: Reaction of ethylene and 18. A 450 mL stainless steel autoclave was dried in an oven at 120° C., and then allowed to cool inside a dry box. After cooling, 4.2 mg (0.0025 mmol) of 18 was added and diluted with toluene (100 mL). The autoclave was sealed, equilibrated to 100° C., and then charged with ethylene (30 bar). After 15 min, the autoclave was vented and the reaction was quenched by addition of MeOH. The solids were filtered, washed with MeOH, and dried under vacuum at 70° C. overnight. The molecular weight and polydispersity were determined by size exclusion chromatography. The extent of branching in the polymer backbone was determined by $^1$H NMR spectroscopy at 120° C. in CDCl$_2$CDCl$_2$.

Example 6—Synthesis of Cationic (PPDA)Ni Complexes

H(OEt$_2$)$_2$BAr$_4^F$ and NiMe$_2$py$_2$ were prepared according to literature procedure of Brookhart et al., *Organometallics*, 2003 11 (11) 3920 and Campora et al., *J. Organomet. Chem.*, 2003, 683, 220, respectively.

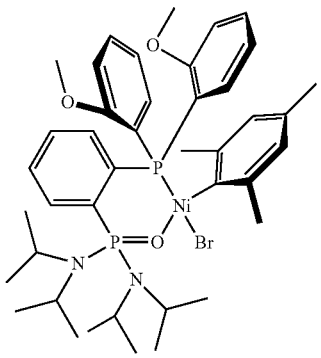

Complex 25

(8) NiBr$_2$ was first formed by stirring the PPDA ligand (8) of Example 2 with Ni(II)bromide ethylene glycol dimethyl ether complex, followed by evaporation of volatiles. 2-Mesitylmagnesium bromide solution (1M in THF, 0.23 mmol) was added to a THF solution of (8) NiBr₂ (0.18 g, 0.23 mmol) at −78° C. The mixture was then slowly warmed to room temperature and stirred for 1 h. The solvent was removed under vacuum. The residue was recrystallized from toluene to give 25 as an orange solid (0.18 g, 93% yield).

¹H NMR (500 MHz, CD₂Cl₂) δ 7.83-7.01 (m, 10H), 6.54 (br, 2H), 5.80 (br, 2H), 3.75 (br, 4H), 3.40 (br, 6H), 2.93 (br, 6H), 2.33 (br, 3H), 1.18 (br, 24H).

¹³C NMR (125 MHz, CD₂Cl₂) δ 160.44, 141.42, 136.34 (d, J=12.8 Hz), 135.38, 135.16 (d, J=9.9 Hz), 134.06 (d, J=15.2 Hz), 132.43 (d, J=8.5 Hz), 131.81 (dd, J=36.1, 5.1 Hz), 129.96, 129.22, 128.75 (d, J=5.7 Hz), 128.41, 128.31, 127.03, 125.49, 123.97, 120.41, 110.11, 47.70 (d, J=6.1 Hz), 27.15, 24.36, 23.86, 19.64.

³¹P NMR (203 MHz, CD₂Cl₂) δ 29.7 (d, J=11.2 Hz), 11.65 (d, J=11.6 Hz).

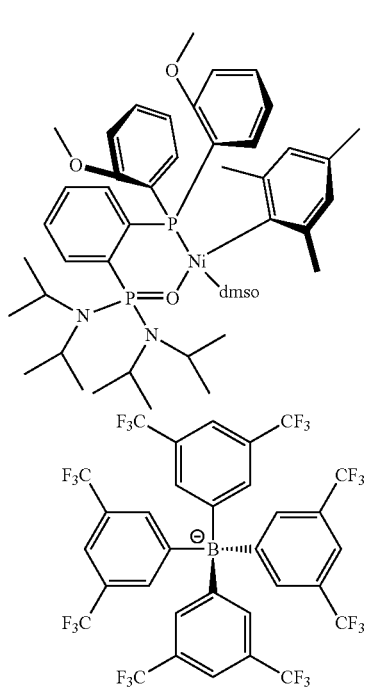

Complex 26

NaBAr$^F_4$ (71 mg, 0.080 mmol) in CH₂Cl₂ was added to a CH₂Cl₂ solution of 25 (66 mg, 0.080 mmol) and DMSO (24 mg, 0.32 mmol). After stirred at room temperature for 1 h, the solvent was removed and the residue was recrystallized from toluene and CH₂Cl₂ to give 26 as an a orange solid (80 mg, 59% yield).

¹H NMR (500 MHz, CD₂Cl₂) δ 7.77 (br, 11H), 7.61 (br, 4H), 7.55-7.40 (m, 5H), 7.05 (br, 2H), 6.62 (br, 2H), 6.01 (br, 2H), 3.87-3.65 (m, 4H), 3.44 (br, 6H), 3.16-2.77 (m, 6H), 2.41-2.22 (m, 6H), 1.95 (br, 3H), 1.19 (br, 24H).

¹³C NMR (125 MHz, CD₂Cl₂) δ 162.26 (q, J=49.8 Hz), 160.60, 143.12, 136.32 (dd, J=12.4, 2.4 Hz), 135.31, 135.06 (d, J=4.9 Hz), 134.18 (d, J=10.5 Hz), 134.04 (d, J=4.5 Hz), 133.72 (d, J=9.4 Hz), 133.47, 132.80 (t, J=9.1 Hz), 129.87 (dd, J=7.1, 2.8 Hz), 129.66 (d, J=2.3 Hz), 129.38 (qq, J=31.5, 2.9 Hz), 125.76, 125.11 (q, J=272.3 Hz), 120.81 (d, J=11.7 Hz), 118.00 (p, J=4.3 Hz), 116.52, 116.08, 110.89, 54.71, 48.14 (d, J=6.0 Hz), 38.54, 26.40, 24.19 (dd, J=44.2, 3.3 Hz), 20.05.

³¹P NMR (203 MHz, CD₂Cl₂) δ 32.31 (d, J=10.9 Hz), 16.71 (d, J=11.2 Hz). HRMS (ESI) m/z calc'd for C41H57N2NiO3P2 (M⁺-DMSO) 745.3198, found 745.3199.

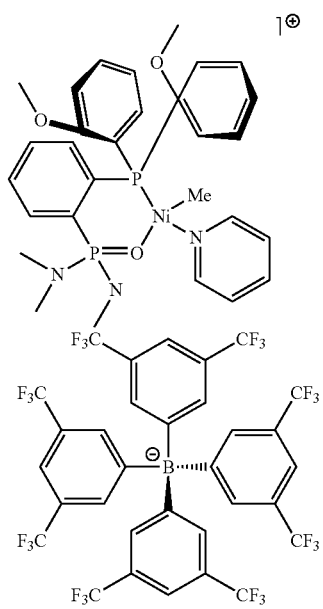

Complex 27

H(OEt₂)₂BAr$^F_4$ (0.25 g, 0.25 mmol) and PPDA ligand (0.11 g, 0.25 mmol) were dissolved in toluene (3 mL). The solution was added into a solution of NiMe₂py₂ (0.068 g, 0.28 mmol) dissolved in toluene (3 mL). After stirring for 4 hours, the dark red solution was filtered to remove black Ni⁰. The solvent was reduced and layered with pentane. The resulting dark brown oil was triturated three times with Et₂O (5 mL) and dried to yield 27 as a light brown solid (0.27 g, 74%).

¹H NMR (500 MHz, CD₂Cl₂) δ$_H$ 8.74 (br, 2H), 7.79-8.0 (br, 6H), 7.72 (s, 8H), 7.56 (s, 4H), 7.31-7.51 (br, 5H), 7.05 (br, 4H), 3.80 (s, 6H), 2.27 (d, J=10 Hz, 12H), −0.95 (d, J=10 Hz, 3H).

¹³C NMR (125 MHz, CD₂Cl₂) δ$_C$ 161.70 (q, J=50 Hz), 160.65, 149.83, 147.20, 137.92, 135.98, 135.17 (d, J=12 Hz), 134.72, 133.557, 132.69, 131.73 (d, J=50 Hz), 130.17 (d, J=11 Hz), 128.83 (d, J=32 Hz), 126.91, 125.64, 124.76, 123.47, 121.00 (d, J=9 Hz), 117.44, 111.42, 55.40, 35.76, −10.60 (d, J=10 Hz).

³¹P NMR (203 MHz, C₆D₆) δ$_P$ 31.1 (d, J=14 Hz), 13.5 (br). HRMS (ESI) m/z calc'd for C25H33N2NiO3P2 (M-pyridine) 529.1909.

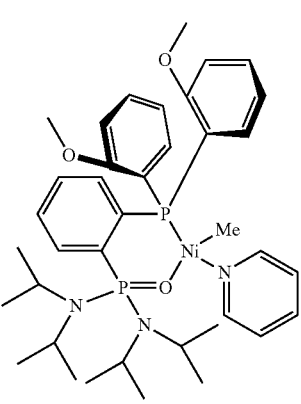

Complex 28

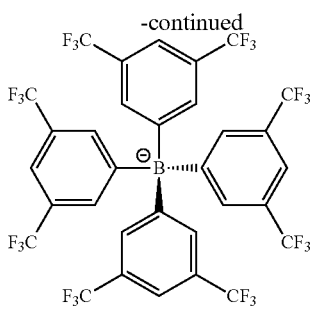

Prepared using a similar procedure as for 27. Complex 28 was isolated as an orange solid (71 mg, 61%).

¹H NMR (300 MHz, CD$_2$Cl$_2$) δ$_H$ 8.44 (s, 8H), 8.13 (br, 1H), 7.76 (m, 4H), 7.73 (m, 2H), 7.42 (m, 1H), 6.85 (m, 2H), 6.78 (t, J=6.0 Hz, 1H), 6.60 (t, J=6.0, 2H), 3.41 (br, 4H), 3.18 (s, 6H), 0.74 (br, 24H), −0.89 (d, J=6.0 Hz, 3H).

¹³C NMR (125 MHz, C$_6$D$_6$) δ$_C$ 150.16, 138.01, 135.90 (d, J=13 Hz), 134.75, 133.57, 133.20, 132.77, 130.51, 129.38, 125.92, 124.92, 123.76, 121.08, 118.52, 117.57 (d, J=35 Hz), 116.63, 116.00, 111.61, 47.33, 29.69, 24.18, 23.38, 22.34, −10.04 (d, J=36 Hz).

³¹P NMR (122 MHz, C$_6$D$_6$) δ$_P$ 30.0 (d, J=12 Hz), 14.2 (br). HRMS (ESI) m/z calc'd for C33H49N2NiO3P2 (M-pyridine) 641.2572.

Complex 29

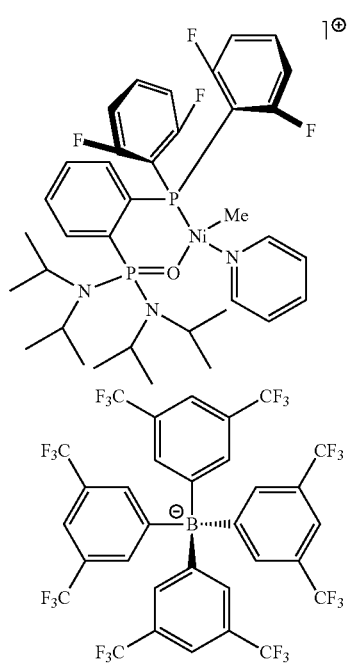

Prepared using a similar procedure as for 27. Complex 29 was isolated as a yellow solid (55 mg, 58%). ¹H NMR (300 MHz, C$_6$D$_6$) δ$_H$ 8.41 (br, 8H), 7.67 (br, 4H), 7.42 (m, 1H), 6.89 (m, 2H), 6.81 (m, 2H), 6.71 (m, 3H), 6.48 (m, 7H), 3.19 (septet, J=6 Hz, 4H), 0.84 (d, J=6 Hz, 12H), 0.67 (d, J=6 Hz, 12H), −0.83 (d, J=9 Hz, 3H).

¹³C NMR (125 MHz, CD$_2$Cl$_2$) δ$_C$ 164.33, 161.71 (q, J=50 Hz), 150.31, 138.45, 135.11, 134.75, 133.31, 131.58, 130.62 (d, J=1 Hz), 128.84 (q, J=31 Hz), 127.79, 125.63, 125.16, 123.46, 121.30, 117.41, 112.80 (d, J=24 Hz), 47.54 (d, J=5 Hz), 23.22 (d, J=1 Hz), 22.56 (d, J=4 Hz), 0.76.

³¹P NMR (203 MHz, C$_6$D$_6$) δ$_P$ 29.0 (d, J=12 Hz), −8.5 (q, J=12 Hz). HRMS (ESI) m/z calc'd for C31H41N2NiOP2 (M-pyridine) 653.1984.

Complex 30

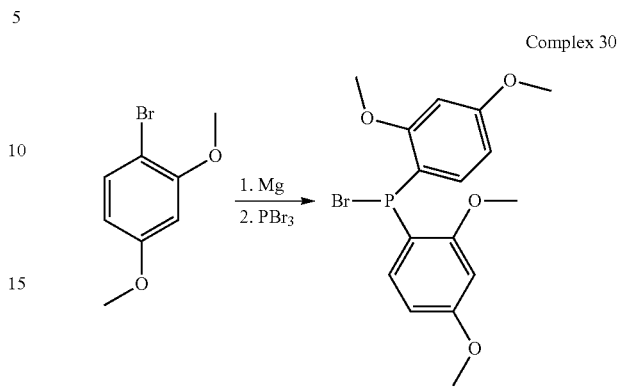

To a round bottom flask containing magnesium turnings (0.49 g, 20.3 mmol) and THF (50 mL) was added a small crystal of iodine. Then, 1-bromo-2,4-dimethoxybenzene (4.0 g, 18 mmol) as a solution in THF (15 mL) was added slowly over 2 hours. After initiation and stirring for 2 hours the solution was transferred by cannula slowly to a solution of PBr$_3$ (2.94 g, 9.21 mmol) in THF (15 mL) at 0° C. The solution was stirred overnight at room temperature, then concentrated to 20 mL total volume, brought into an inert atmosphere glovebox, and filtered through Celite. Solvent was removed by vacuum to yield 5.3 g of crude bromobis(2,4-dimethoxyphenyl)phosphine which was used in subsequent reactions without further purification.

¹H NMR (500 MHz, CDCl$_3$) δ 7.33 (dd, J=8.5, 3.6 Hz, 1H), 6.52 (dd, J=8.5, 2.3 Hz, 1H), 6.45 (dd, J=4.8, 2.3 Hz, 1H), 3.82 (s, 6H).

³¹P NMR (121 MHz, CDCl$_3$) δ$_P$ 70.10.

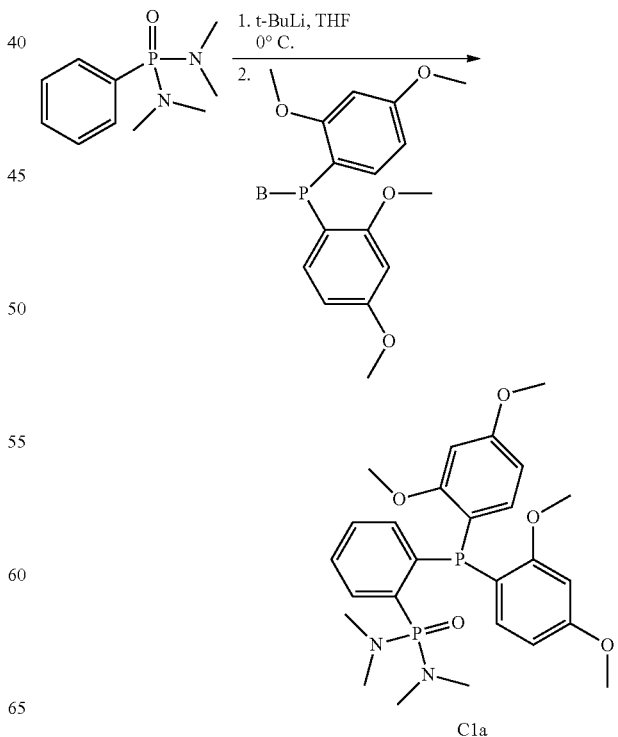

C1a

To a solution of N,N,N',N'-tetramethyl phenylphosphonic diamide (0.20 g, 0.94 mmol) in THF (20 mL) was added t-BuLi (0.72 mL, 1.22 mmol, 1.7 M in pentane) at 0° C. and stirred for 30 min. A THF solution of bis(2,4-dimethoxyphenyl)bromophosphine (0.40 g, 1.0 mmol, 6.0 mL solution) was added to the reaction mixture and then warmed slowly to room temperature and stirred for 30 min. The desired PPDA ligand C1a (0.15 g, 30.8% yield) was isolated as a 2:1 mixture with N,N,N',N'-tetramethyl phenylphosphonic diamide as a white solid by silica gel column chromatography with $CH_2Cl_2$/MeOH (95:5) as eluent. This mixture was carried forward without additional purification.

$^1$H NMR (300 MHz, $CDCl_3$) δ 8.24 (m, 1H), 7.42 (m, 1H), 7.34 (m, 1H), 7.10 (m, 1H), 6.49 (m, 4H), 6.39 (m, 2H), 3.81 (s, 6H), 3.68 (s, 6H), 2.55 (d, J=10 Hz).

$^{31}$P NMR (121 MHz, $CDCl_3$) $δ_P$ 30.57 (d, J=0.9 Hz), 29.64 (s, residual phosphonic diamide starting material), −30.69 (br).

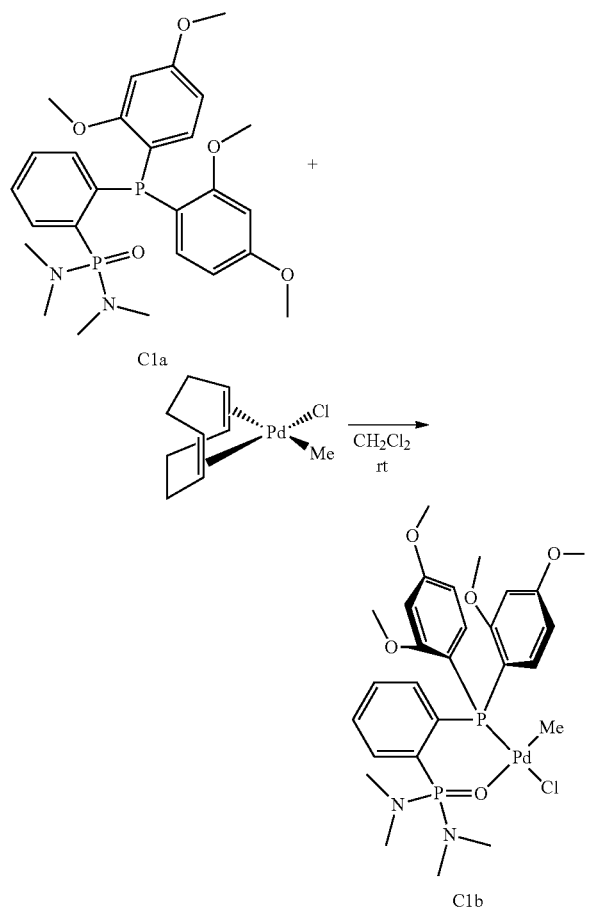

C1a (0.10 g, 0.19 mol) and ($η^2,η^2$-cyclooctadi-1,5-ene)(chloro)(methyl)palladium (0.05 g, 0.19 mmol) were weighed into a small vial and then dissolved in dichloromethane (3 mL) at room temperature. The solution was stirred for 10 min. Pentane was layered on top of the solution. After standing overnight, the mother liquor was decanted, the solids were washed with pentane, then dried under vacuum to afford C1b (0.11 g, 84% yield) as a yellow solid. This complex was carried forward without additional purification.

$^1$H NMR (501 MHz, $CDCl_3$) δ 7.50 (m, 3H), 7.37 (m, 2H), 6.44 (br, 5H), 3.82 (s, 6H), 3.55 (b, 6H), 2.57 (br, 12H), 0.42 (d, J=9.0 Hz, 3H).

$^{31}$P NMR (203 MHz, $CDCl_3$) $δ_P$ 33.41 (d, J=10 Hz), 21.57 (d, J=9.0 Hz).

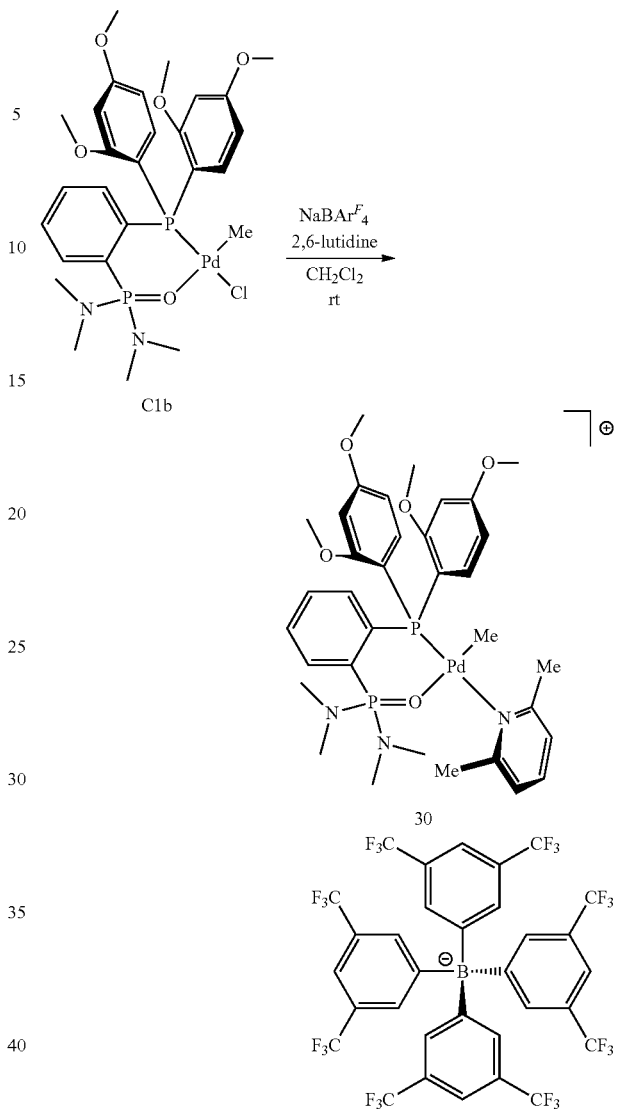

C1b (66 mg, 0.074 mmol) and 2,6-lutidine (9 mg, 0.084 mmol) were weighed into a small vial and then dissolved in dichloromethane (5 mL). After dissolution, the solution was added to a flask containing sodium tetrakis[3,5-bis(trifluoromethyl)phenyl]borate (50 mg, 0.074 mmol) cooled to −78° C. The mixture was slowly warmed to room temperature with vigorous stirring over 30 min. The solids were removed by filtration through Celite, and the filtrate was concentrated to ca. 2 mL and then the solution was diluted with toluene (10 mL). After standing overnight, the precipitate was filtered and washed with pentane, then dried under vacuum to afford 30 (71 mg, 58% yield) as a pale yellow solid.

$^1$H NMR (501 MHz, $CDCl_3$) δ 7.70 (m, 8H, $BAr^F$), 7.61 (t, J=9 Hz, 1H), 7.51 (m, 4H, $BAr^F$), 7.47 (m, 3H), 7.38 (m, 1H), 7.15 (m, 2H), 6.96 (m, 1H), 6.58 (m, 5H), 3.85 (s, 6H), 3.56 (br, 6H), 3.05 (br, 6H), 2.52 (s, 6H), 2.24 (b, 12H), −0.10 (d, J=3 Hz, 3H).

$^{13}$C NMR (126 MHz, $CDCl_3$) δ 161.81 (dd, J=99.7, 49.8 Hz), 138.67, 136.38 (d, J=11.4 Hz), 135.96 (dd, J=47.5, 8.0 Hz), 134.91, 132.68 (t, J=10.3 Hz), 132.43, 131.27 (d, J=18.1 Hz), 130.95 (dd, J=7.4, 2.5 Hz), 130.25-129.86 (m), 129.00 (qdd, J=31.4, 5.7, 2.8 Hz), 127.91, 125.75, 123.58, 122.87, 121.41, 117.58, 105.44, 98.88, 55.65, 55.12 (d, J=50.5 Hz), 36.16 (d, J=170.8 Hz), 26.20 (d, J=81.6 Hz), −2.62.

$^{31}$P NMR (203 MHz, CDCl$_3$) δ$_P$ 33.64 (d, J=18.0 Hz), 21.59 (d, J=18.0 Hz). HRMS (ESI) m/z calc'd for C27H37N2O5P2Pd+ (M-Lutidine) 637.1207, found 637.1198.

Complex 31

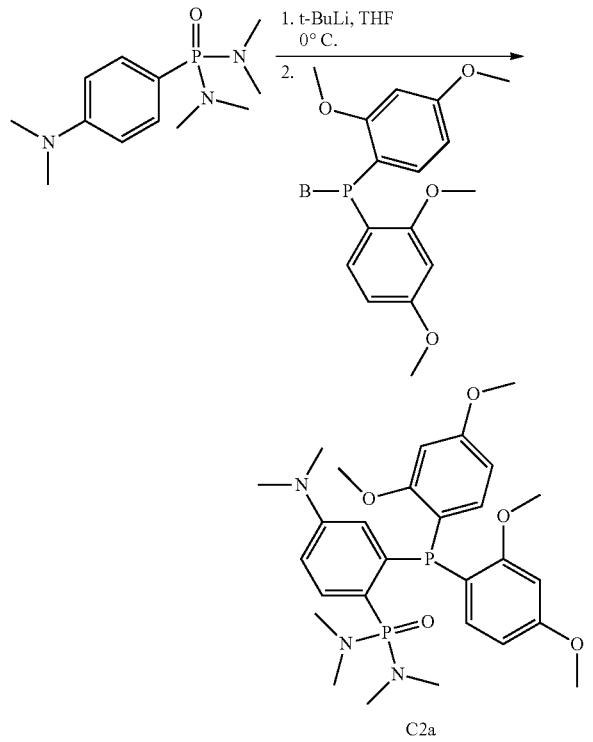

To a solution of N,N,N',N'-tetramethyl 4-(N,N-dimethyl-aminophenyl)phosphonic diamide (0.20 g, 0.78 mmol) in THF (20 mL) was added t-BuLi (0.6 mL, 1.0 mmol, 1.7 M in pentane) at 0° C. and stirred for 30 min. A THF solution (5 mL) of bis(2,4-dimethoxyphenyl)bromophosphine (0.33 g, 0.86 mmol) was added to the reaction mixture and then warmed slowly to room temperature then stirred for 30 min. The desired product C2a (0.11 g, 25.1% yield) was isolated as a 2:1 mixture with residual N,N,N',N'-tetramethyl 4-(N, N-dimethylaminophenyl)phosphonic diamide as a yellow solid after silica gel column chromatography with dichloromethane/MeOH (95:5) as eluent. This mixture was carried forward without further purification.

$^1$H NMR (300 MHz, CDCl$_3$) δ 8.07 (m, 1H), 7.61 (m, 1H), 6.54 (m, 2H), 6.47 (m, 2H), 6.40 (m, 3H), 3.81 (s, 6H), 3.70 (s, 6H), 2.77 (s, 6H), 2.53 (br, 12H).

$^{31}$P NMR (121 MHz, CDCl$_3$) δ 32.05 (d, J=1.3 Hz), 31.38 (s, residual phosphonic diamide starting material), −29.42 (br).

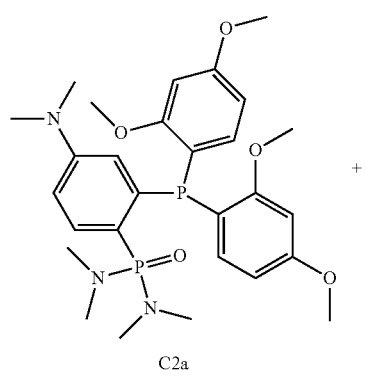

C2a

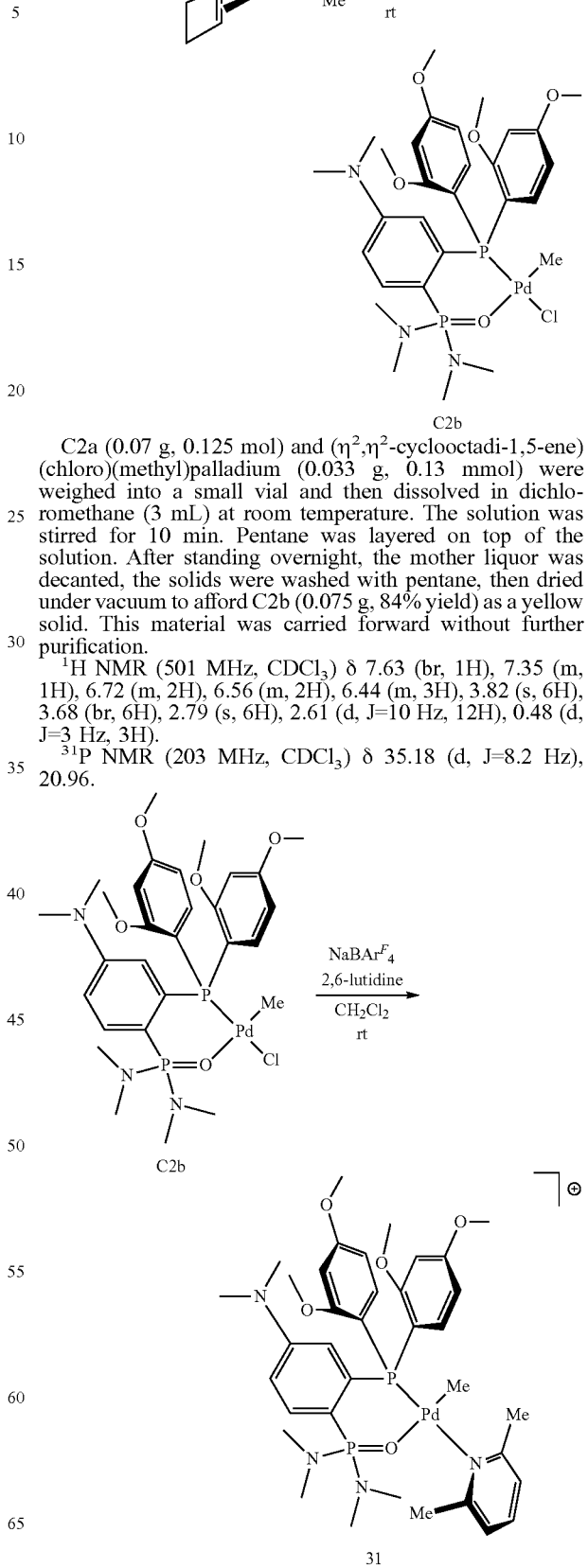

C2a (0.07 g, 0.125 mol) and (η$^2$,η$^2$-cyclooctadi-1,5-ene)(chloro)(methyl)palladium (0.033 g, 0.13 mmol) were weighed into a small vial and then dissolved in dichloromethane (3 mL) at room temperature. The solution was stirred for 10 min. Pentane was layered on top of the solution. After standing overnight, the mother liquor was decanted, the solids were washed with pentane, then dried under vacuum to afford C2b (0.075 g, 84% yield) as a yellow solid. This material was carried forward without further purification.

$^1$H NMR (501 MHz, CDCl$_3$) δ 7.63 (br, 1H), 7.35 (m, 1H), 6.72 (m, 2H), 6.56 (m, 2H), 6.44 (m, 3H), 3.82 (s, 6H), 3.68 (br, 6H), 2.79 (s, 6H), 2.61 (d, J=10 Hz, 12H), 0.48 (d, J=3 Hz, 3H).

$^{31}$P NMR (203 MHz, CDCl$_3$) δ 35.18 (d, J=8.2 Hz), 20.96.

-continued

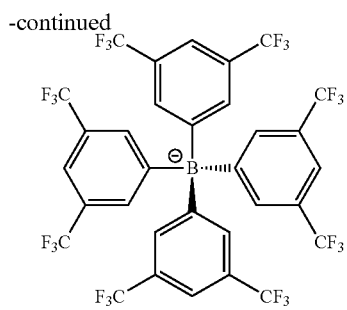

C2b (49 mg, 0.056 mmol) and 2,6-lutidine (7 mg, 0.06 mmol) were weighed into a small vial and then dissolved in dichloromethane (5 mL). After dissolution, the solution was added to a flask containing sodium tetrakis[3,5-bis(trifluoromethyl)phenyl]borate (40 mg, 0.056 mmol) cooled to −78° C. The mixture was slowly warmed to room temperature with vigorous stirring over 30 min. The solids were removed by filtration through Celite, and the filtrate was concentrated to ca. 2 mL and then the solution was diluted with toluene (10 mL). After standing overnight, the precipitate was filtered and washed with pentane, then dried under vacuum to afford 31 (80 mg, 87% yield) as a yellow solid.

$^1$H NMR (501 MHz, CDCl$_3$) δ 7.70 (m, 8H, BAr$^F$), 7.61 (m, 1H), 7.51 (m, 4H, BaR$^F$), 7.15 (m, 2H), 6.72 (m, 3H), 6.48 (br, 3H), 3.84 (s, 6H), 3.64 (br, 6H), 3.06 (s, 6H), 2.81 (s, 6H), 2.26 (br, 12H), −0.08 (d, J=3.5 Hz, 1H).

$^{13}$C NMR (126 MHz, CDCl$_3$) δ 161.81 (dd, J=99.7, 49.9 Hz), 151.40 (dd, J=8.4, 2.4 Hz), 138.53, 136.18 (dd, J=47.1, 9.6 Hz), 134.91, 134.72 (t, J=11.5 Hz), 129.74-128.46 (m), 127.91, 125.75, 124.35, 123.58, 122.77 (d, J=3.0 Hz), 121.41, 119.24 (dd, J=12.1, 5.0 Hz), 117.58, 116.28 (d, J=18.3 Hz), 114.95 (d, J=18.3 Hz), 111.88 (d, J=16.0 Hz), 107.04 (d, J=59.7 Hz), 105.31, 98.68, 55.63, 55.31, 39.66, 36.16, 26.15, −2.76.

$^{31}$P NMR (203 MHz, CDCl$_3$) δ 35.27 (d, J=16.0 Hz), 21.63 (br).

HRMS (ESI) m/z calc'd for C27H37N2O5P2Pd+ (M-Lutidine) 680.16290, found 680.16282.

Example 7—Polymerization of Ethylene by (PPDA)Ni Complexes

A 450 mL stainless steel autoclave was dried in an oven at 120° C., and then allowed to cool inside the dry box. After cooling, toluene (300 mL) and an aliquot of catalyst 27 stock solution (1.35 μmol) was added. The autoclave was then sealed, stirred in a heated oil bath. After the inner temperature reached 95° C., the autoclave was charged with ethylene (30 bar) and stirred for 15 min. The autoclave exothermed to 117° C. The reaction was then quenched by addition of MeOH. The mixture was filtered and washed with MeOH. The solids were dried under vacuum at 80° C. overnight to afford 19.20 g polyethylene. The molecular weight and polydispersity were determined by size exclusion chromatography. The extent of branching in the polymer backbone was determined by $^1$H NMR spectroscopy.

| Catalyst | $T_{max}$ (° C.)$^a$ | yield (g) | Activity [×10$^{-6}$ g (mol Ni)$^{-1}$ h$^{-1}$] | TOF (×10$^{-6}$ h$^{-1}$) | $M_w$ (×10$^{-3}$ g mol$^{-1}$)$^b$ | Đ ($M_w$/$M_n$)$^b$ | Me br$^c$ |
|---|---|---|---|---|---|---|---|
| 26$^d$ | | 11.4 | 27 | 0.98 | 170 | 2.6 | 2.2 |
| 27 | 117 | 19.2 | 57 | 2.0 | 21 | 1.7 | 1.5 |
| 28 | 109 | 11.2 | 33 | 1.2 | 170 | 2.2 | n.d.$^e$ |
| 29 | 100 | 3.1 | 9.3 | 0.33 | 99 | 1.6 | n.d.$^e$ |

$^a$Maximum temperature during polymerization due to reaction exotherm.
$^b$Absolute molecular weight and polydispersity determined by GPC analysis with triple detection.
$^c$Methyl branches per 1000 carbons as determined by $^1$H or quantitative $^{13}$C NMR spectroscopy.
$^d$Conditions: 26 (1.25 μmol) and C$_2$H$_4$ (30 bar) were stirred in toluene (0.2 L) at 100° C. for 20 min.
$^e$Not determined.

Example 8—Polymerization of Ethylene by a (PPDA)Ni Complexes in Presence of Functional Additive A 450 mL stainless steel autoclave was dried in an oven at 120° C., and then allowed to cool inside the dry box. After cooling, toluene (300 mL), an aliquot of catalyst 27 stock solution (1.35 μmol) and MEHQ (0.25 g, 1500 equiv.) was added. The autoclave was then sealed, stirred in a heated oil bath. After the inner temperature reached 100° C., the autoclave was charged with ethylene (30 bar) and stirred for 15 min. The reaction was then quenched by addition of MeOH. The mixture was filtered and washed with MeOH. The solids were dried under vacuum at 80° C. overnight to afford 10.42 g polyethylene. The molecular weight and polydispersity were determined by size exclusion chromatography.

| Additive | Equiv | Yield (g) | Av TOF [mol (mol Ni)$^{-1}$ h$^{-1}$] | $k_{rel}$ | $M_w$ (×10$^{-3}$ g mol$^{-1}$)$^a$ | Đ ($M_w$/$M_n$)$^a$ |
|---|---|---|---|---|---|---|
| None | — | 18.6 | 2,000,000 | 1 | 26 | 1.7 |
| MEHQ | 1500 | 18.6 | 2,000,000 | 1 | 23 | 1.5 |
| Et$_2$O | 1500 | 10.4 | 1,100,000 | 0.6 | 26 | 1.7 |
| Ethyl acetate | 1500 | 17.9 | 1,900,000 | 1 | 24 | 1.7 |
| H$_2$O | 1250 | 11.4 | 1,200,000 | 0.6 | 26 | 1.7 |
| NEt$_3$ | 1500 | 0.07 | 7,400 | 0.004 | — | — |
| O$_2$ | (1 atm) | 0 | 0 | 0 | — | — |

$^a$Absolute molecular weight and polydispersity determined by GPC analysis with triple detection.

As provided in this Example 8, polymerization continued in the presence of the functional additives known to disrupt and/or preclude ethylene polymerization with prior transition metal catalysts.

Example 9—Productivity of Over Time Using Complex 27

A 450 mL stainless steel autoclave was dried in an oven at 120° C., and then allowed to cool inside the dry box. After cooling, toluene (300 mL) and an aliquot of catalyst 27 stock solution (1.35 μmol) was added. The autoclave was then sealed, stirred in a heated oil bath. After the inner temperature reached 100° C., the autoclave was charged with ethylene (3.5 bar) and stirred for 15 min. The reaction was then quenched by addition of MeOH. The mixture was filtered and washed with MeOH. The solids were dried under vacuum at 80° C. overnight to afford polyethylene. The molecular weight and polydispersity were determined by size exclusion chromatography.

| Entry | time (h) | yield (g) | Productivity [kg (mol Ni⁻¹)] | TOF ($\times 10^{-3}$ h⁻¹) | $M_w$ ($\times 10^{-3}$ g mol⁻¹)[a] | $Đ$ ($M_w/M_n$)[a] |
|---|---|---|---|---|---|---|
| 1 | 0.25 | 0.90 | 670 | 95 | 15 | 2.0 |
| 2 | 0.5 | 1.4 | 1000 | 76 | 16 | 1.7 |
| 3 | 1 | 3.1 | 2300 | 83 | 16 | 1.8 |
| 4 | 1.5 | 3.9 | 2900 | 68 | 17 | 1.6 |
| 5 | 2 | 4.3 | 3200 | 57 | 120 | 1.8 |

[a]Absolute molecular weight and polydispersity determined by GPC analysis with triple detection.

Example 10—Copolymerization of Ethylene and Polar Monomer Catalyzed by a (PPDA)Ni Complex A 25 mL stainless steel autoclave was dried in an oven at 120° C., and then allowed to cool inside the dry box. After cooling, an aliquot of catalyst 27 stock solution (10 µmol) and butyl vinyl ether (1.94 mL, 15 mmol) were diluted with toluene to 15 mL. The autoclave was then sealed, stirred in a heated oil bath. The autoclave was charged with ethylene (30 bar), heated to 100° C. and stirred for 12 hours. The reaction was then quenched by addition of MeOH. The mixture was filtered and washed with MeOH. The solids were rinsed with chloroform to remove any poly(butyl vinyl ether) and dried under vacuum at 80° C. overnight to afford 0.65 g polyolefin. The molecular weight and polydispersity were determined by size exclusion chromatography. The percent incorporation of functional monomer in the polymer backbone was determined by ¹H NMR spectroscopy.

| Catalyst | yield (g) | Activity [$\times 10^{-3}$ g (mol Ni)⁻¹ h⁻¹] | $M_w$ ($\times 10^{-3}$ g mol⁻¹)[a] | $Đ$ ($M_w/M_n$)[a] | % incorp.[b] |
|---|---|---|---|---|---|
| 27 | 0.65 | 5.4 | 9.4 | 2.0 | 0.05 |

[a]Absolute molecular weight and polydispersity determined by GPC analysis with triple detection.
[b]Methyl branches per 1000 carbons as determined by quantitive ¹³C NMR spectroscopy.

Example 11—Polymerization of Ethylene by (PPDA)Ni Complexes

A 25 mL stainless steel autoclave was dried in an oven at 120° C., and then allowed to cool inside the dry box. After cooling, toluene (10 mL) and 30 (1.25 µmol, 2.0 mg) was added. The autoclave was then sealed and stirred in a heated oil bath. After the inner temperature reached 100° C., the autoclave was then charged with ethylene (30 bar) and stirred for 15 min. The reaction was then quenched by addition of MeOH. The mixture was filtered and washed with MeOH. The solids were dried under vacuum at 100° C. overnight to afford 0.52 g white solid. The molecular weight and polydispersity were determined by size exclusion chromatography. The extent of branching in the polymer backbone was determined by ¹H-NMR spectroscopy. The same procedure was repeated for 31.

Example 12—Copolymerization of Ethylene and Polar Monomer by (PPDA)Ni Complexes A 25 mL stainless steel autoclave was dried in an oven at 120° C., and then allowed to cool inside the dry box. After cooling, toluene (12 mL) 30 (10.5 µmol, 17.0 mg) and methyl acrylate (3 mL, 33.1 mmol) was added. The autoclave was then sealed and stirred in a heated oil bath. After the inner temperature reached 100° C., the autoclave was then charged with ethylene (30 bar) and stirred for 12 hrs. The reaction was then quenched by addition of MeOH. The mixture was filtered and washed with MeOH. The polymer was redissolved in 10 mL toluene and precipitated again by the addition of MeOH. The solids were dried under vacuum at 100° C. overnight to afford 1.03 g white solid. The molecular weight and polydispersity were determined by size exclusion chromatography. The comonomer incorporation was determined by ¹H-NMR spectroscopy. The same procedure was repeated for 31.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of polymerization comprising:
providing a reaction mixture including olefin monomer, polar monomer and transition metal complex of Formula (II):

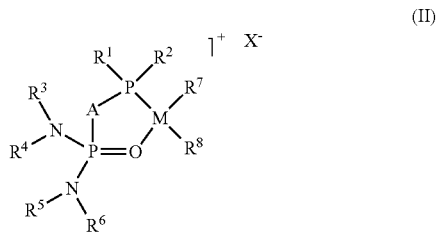

(II)

wherein M is a transition metal, A is selected from the group consisting of alkylene, alkenylene, arylene and heteroarylene, and wherein $R^1$, $R^2$, $R^3$, $R^4$, $R^5$ and $R^6$ are independently selected from the group consisting of alkyl, heteroalkyl, cycloalkyl, heterocycloalkyl, aryl, heteroaryl, alkyl-aryl and alkyl-heteroaryl, wherein $R^1$ and $R^2$ optionally form a ring structure and any combination of $R^3$, $R^4$, $R^5$ and/or $R^6$ optionally form a ring structure and wherein $R^7$ is selected from the group consisting of alkyl and aryl and $R^8$ is selected from the group consisting of amine, heteroaryl, monophosphine, halo and sulfoxide and wherein $X^-$ is a non-coordinating counter anion; and
copolymerizing the olefin monomer with the polar monomer in the presence of the transition metal complex.

2. The method of claim 1, wherein the polar monomer is selected from the group consisting of acrylic acid, alkyl acrylic acids, alkyl acrylates, acetates, acrylamide, vinyl ethers and/or acrylonitrile.

3. The method of claim 2, wherein the olefin monomer is ethylene or propylene.

4. The method of claim 1, wherein M is palladium.

5. The method of claim 1, wherein M is nickel.

6. The method of claim 1, wherein copolymer resulting from the copolymerization has molecular weight ($M_w$) of at least 5,000 Da.

7. The method of claim 1, wherein copolymer resulting from the copolymerization has molecular weight ($M_w$) of at least 10,000-200,000 Da.

8. The method of claim 1, wherein at least 50 percent of the polar monomer in the copolymer is incorporated in-chain.

9. The method of claim 1, wherein at least 90 percent of the polar monomer in the copolymer is incorporated in-chain.

10. The method of claim 1, wherein the polar monomer is exclusively incorporated in-chain.

11. The method of claim 1, wherein M is palladium or nickel, A is arylene, $R^1$-$R^2$ are independently aryl, $R^3$-$R^6$ are independently alkyl, $R^7$ is selected from alkyl and aryl and $R^8$ is selected from the group consisting of heteroaryl, halo and sulfoxide.

12. The method of claim 1, wherein 3-15 mol. % polar monomer is incorporated into the copolymer.

13. The method of claim 8, wherein 5-15 mol. % polar monomer is incorporated into the copolymer.

\* \* \* \* \*